(12) United States Patent
Kim et al.

(10) Patent No.: US 7,517,683 B2
(45) Date of Patent: Apr. 14, 2009

(54) HIV-LIKE PARTICLES AND THE USE THEREOF

(75) Inventors: Chul Joong Kim, Daejeon (KR); Eun Kim, Daejeon (KR); Kwang Soon Shin, Daejeon (KR); Hyun Soo Kim, Daejeon (KR)

(73) Assignee: The Industry and Academic Cooperation in Chungnam National University, Daejeon (KR)

( * ) Notice: Subject to any disclaimer, the term of this patent is extended or adjusted under 35 U.S.C. 154(b) by 179 days.

(21) Appl. No.: 10/466,134

(22) PCT Filed: Jan. 8, 2002

(86) PCT No.: PCT/KR02/00031

§ 371 (c)(1),
(2), (4) Date: Jul. 8, 2003

(87) PCT Pub. No.: WO02/053757

PCT Pub. Date: Jul. 11, 2002

(65) Prior Publication Data

US 2004/0131592 A1      Jul. 8, 2004

(30) Foreign Application Priority Data

Jan. 8, 2001      (KR) ................... 2001-894

(51) Int. Cl.
*C12N 15/86* (2006.01)
*C12N 15/09* (2006.01)
*C12N 5/10* (2006.01)
*A61K 31/7105* (2006.01)
*A61K 31/713* (2006.01)

(52) U.S. Cl. ............... 435/320.1; 435/69.3; 435/325; 435/235.1; 514/44

(58) Field of Classification Search ............. 435/5, 435/235.1, 6; 424/204.1, 199.1, 93.2
See application file for complete search history.

(56) References Cited

U.S. PATENT DOCUMENTS 5,770,428 A      6/1998   Boris-Lawrie (Continued)

FOREIGN PATENT DOCUMENTS

EP      0 753 581 A1      1/1997

(Continued)

OTHER PUBLICATIONS

Bray et al., "A small element from the Mason Pfizer monkey virus genome makes human immunodeficiency virus type 1 expression and replication Rev-independent," Proc. Natl. Acad.Sci., vol. 91, pp. 1256-1260 (1994).*

(Continued)

*Primary Examiner*—Mary E Mosher
(74) *Attorney, Agent, or Firm*—Joseph Hyosuk Kim; JHK Law

(57) ABSTRACT

Disclosed are alphavirus-based expression vectors expressing env, gag, pro, and/or pol genes of HIV-1, their transcripts, and transformed host cells. The present invention describes the expression of the Gag, Env, Pol, and/or Pro Proteins using the above expression vectors, and HIV-like particles (HIV-LPs) composed of the above recombinant proteins. The virus-like particles (VLPs) of the present invention, as the mature and infective particles, are very useful as an antigen for a diagnostic kit for HIV infection as well as for a vaccine composition for prevention of HIV infection.

10 Claims, 32 Drawing Sheets

U.S. PATENT DOCUMENTS 5,843,723 A * 12/1998 Dubensky et al. .......... 435/69.3
6,054,566 A *  4/2000 Donson et al. ............. 536/23.1
6,893,866 B1 *  5/2005 Westaway et al. ........ 435/320.1

FOREIGN PATENT DOCUMENTS

WO      WO 97/31115 A2      8/1997
WO      WO 99/28487    *    6/1999
WO      WO 00/39304 A2      7/2000

OTHER PUBLICATIONS

Caley et al., "Humoral, Mucosal, and Cellular Immunity in Response to a Human Immunodeficiency Virus Type 1 Immunogen Expressed by a Venezuelan Equine Encephalitis Virus Vaccine Vector," Journal of Virology, vol. 71, No. 4, pp. 3031-3038 (1997).*

Fang et al., "Efficient Human Immunodeficiency Virus (HIV)-1 Gag-Env Pseudovirion Formation Elicited from Mammalian Cells by a Canarypox HIV vaccine candidate," The Journal of Infectious Diseases, 180: 1122-1132 (1999).*
Park et al., "Mutations in the Protease Gene of Human Immunodeficiency Virus Type 1 Affect Release and Stability of Virus Particles," Virology, vol. 194, Issue 2, pp. 843-850, Jun. 1993.*
Haffar et al. Journal of Virology 64:2653-2659, 1990.*
Fang, Z.Y. et al., 1999, *J. Infect. Dis.*, 180(4): 1122-1132.
Staropoli, I. et al., 2000, *J. Biol. Chem.*, 275(45):35137-35145.
Cimarelli, A. et al., 2000, *J. Virol.*, 74(7):3046-3057.
Berglund, P. et al., 1999, *Vaccine*, 17:497-507.
Muriaux, D. et al., 2001, *Proc. Natl. Acad. Sci.*, 98(9):5246-5251.
Clever, J. L. et al., 2000, *J. Virol.*, 74(1):541-546.
VanCoti, T. C. et al., 1999, *J. Virol.*, 73(6):4640-4650.
Schnell, M. J. et al., 2000, *Proc. Natl. Acad. Sci.*, 97(7):3544-3549.
McBride, M. S. et al., 1997, *J. Virol.*, 71(6):4544-4554.
Gundlach, B. R. et al., 2000, *J. Virol.*, 74(8):3537-3542.

* cited by examiner

A

B 1 2 3        4 5 6

SEQUENCE LISTING

<160> NUMBER OF SEQ ID NOS: 21

<210> SEQ ID NO 1
<211> LENGTH: 39
<212> TYPE: DNA
<213> ORGANISM: Artificial Sequence
<220> FEATURE:
<223> OTHER INFORMATION: Primer

<400> SEQUENCE: 1
gcggatcccg ggatgggtgc gagagcgtca atattaagt                          39

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
cgcggatccc tgttactgtg acaaggggtc gttgccaaa                          39

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
cgcggatccc tgcagttaaa gtacaaccaa tctgagtcaa ca                      42

<210> SEQ ID NO 4
<211> LENGTH: 42
<212> TYPE: DNA
<213> ORGANISM: Artificial Sequence
<220> FEATURE:
<223> OTHER INFORMATION: Primer

<400> SEQUENCE: 4
cgcgcctcga gcgggatccc atgagagtga aggggacacg ga                      42

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
aatggatcct atagcaaagc cctttccaag ccc                                33

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cccaagcttt tagcatgctg tcatcatttc                                    30

<210> SEQ ID NO 7
<211> LENGTH: 34

```
<212> TYPE: DNA
<213> ORGANISM: Artificial Sequence
<220> FEATURE:
<223> OTHER INFORMATION: Primer

<400> SEQUENCE: 7
ggttctgcag aagcttcctt gttatttcaa acca                          34

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
cccaagcttc atcaggcctt atcacct                                  27

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
tcccccggga agcttgcgca gcagcatctg ttg                           33

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
ccaagatcta tgacagcctc ctcctttagt ttc                           33

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
caacccgggt cgcgattaag tgtcaatagg actaat                        36

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
ccggatatca cctctacggc ggtccta                                  27

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
```
cgcccgggtt actgtgacaa ggggtcgttg ccaaa                                35

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
aatggatccc ctccctgtg agctagact                                       29

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
aatgatatca gatctccaag acatcatccg ggcaa                               35

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
aataggcctg tctttcagtg cagtctt                                        27

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
cacaggccta tagggaaaat ctggccttc                                      29

<210> SEQ ID NO 18
<211> LENGTH: 20
<212> TYPE: DNA
<213> ORGANISM: Artificial Sequence
<220> FEATURE:
<223> OTHER INFORMATION: Frame shift part of Gag-pol

<400> SEQUENCE: 18
caggctaatt ttttagggaa                                                20

<210> SEQ ID NO 19
<211> LENGTH: 15
<212> TYPE: DNA
<213> ORGANISM: Artificial Sequence
<220> FEATURE:
<223> OTHER INFORMATION: Part of HIV genomic DNA

<400> SEQUENCE: 19
caggcctata gggaa                                                     15

<210> SEQ ID NO 20
<211> LENGTH: 27
<212> TYPE: DNA
<213> ORGANISM: Artificial Sequence

```
<220> FEATURE:
<223> OTHER INFORMATION: Primer

<400> SEQUENCE: 20
ttaggatcca tgggtgcgag agcgtca                                              27

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
cgcggatccc taatcctcat tctgtctacc                                           30
```

HIV-LIKE PARTICLES AND THE USE THEREOF

CONTINUING DATA

The present application is a U.S. national phase application under 35 U.S.C. §371, of PCT/KR02/00031, filed Jan. 8, 2002.

TECHNICAL FIELD

The present invention relates to an expression vector which expresses Gag protein of HIV, an expression vector which expresses Env protein of HIV, an expression vector which expresses both Gag and Env proteins simultaneously, an expression vector which expresses Gagpol polyprotein of HIV and an expression vector which expresses both Gagpol polyprotein and Env protein simultaneously.

BACKGROUND ART

Human Immunodeficiency Virus (HIV) is known as the causative agent of Acquired Immunodeficiency Syndrome (AIDS). Especially, HIV-1 and HIV-2 belongs to the subgroup *Lentivirdae* of retroviruses, which carry a single-stranded RNA. Once in a susceptible host cell, the RNA genome is reverse-translated by viral reverse transcriptase to generate double-stranded DNA, which becomes integrated into the host's chromosome, resulting in provirus.

In order to better understand the background of the present invention, with reference to FIG. 1, there is given the structure of the HIV-1 genome 9.2 kb in size. The HIV-1 genome possesses structural genes consisting of gag, pol and env, and accessory genes including tat, rev, nef, vif, vpu and vpx.

A HIV Gag polyprotein precursor, Pr55gag, is expressed from full-length gag-pol RNA with a size of 55 kDa. A HIV Gag precursor is transported to the inner surface of the cell plasma membrane by a N-terminal myristate moiety, where directing the assembly of virions. Maturation of virions requires the proteolytic cleavage of the Pr55gag by protease (Pro) encoded by the pol gene of HIV into matrix (MA, p17), capsid (CA, p24), nucleocapsid (NA, p9) and p6 proteins (Gheysen D et al, Cell, 59, 103-112 (1989); Bray, M. et al. Proc. Natl. Acad. Sci. USA 91, 1256-1260 (1994); Cann, A. J., and J. Karn, AIDS 3 (Suppl.1), S19-S34 (1989); Ratner, L., W. et al., Nature 313, 277-284 (1985); Wain-Hobson, S. et al., Cell 40, 9-17 (1985)).

The envelope glycoprotein (Env) precursor, gp160, is expressed from the spliced RNA. In virus-infected cells, the precursor is cleaved by protease from the host or the virus into gp120 subunit at the N-terminal side and gp41 subunit at the C-terminal side, which are properly targeted to a plasma membrane with anchorage on the external surface and insertion into the cell membrane, respectively. In the mature virion, gp120 and gp41 subunits form a heterodimer in which the two subunits are non-covalently associated, which is known to be directly responsible for the infectivity, cellular tropism and cytopathogenicity of HIV (Robey, E. and Axel, R., Cell 60, 697-700 (1990)). Because of the close relation to immunogenicity, the Env protein of HIV is a target for the development of the HIV vaccines.

The protease (Pro) is produced from self-cleavage of Pr160 gag-pol precursor, translated by ribosomal frame shift at 3' end of gag mRNA region while translating gag-pol mRNA (Jacks, T. and Varmus, H. E. Science 230, 1237-1242 (1985); Jacks, T. et al, Nature 331, 280-283 (1988); Sonigo, p. et al, Cell 45, 375-385 (1986)). The protease participates in the processing of the Pr160gag-pol polyprotein and env protein, resulting in mature infectious virions (Kohl, N. et al., Proc. Natl. Acad. Sci. USA 85, 4686-4690 (1988)).

To data, suggested AIDS vaccines include inactivated vaccines, attenuated vaccines, recombinant live vaccines, virus-like particle vaccines, and subunit vaccines.

The inactivated whole virus vaccines are prepared by chemically or physically treating isolated viral particles to destroy their infectivity. This kind of vaccine is easy to prepare and is capable of using most epitopes, in contrast, it may cause diseases when the virus is not completely inactivated, on the other hand, the strong treatment for the complete inactivation may cause destruction of many epitopes. Although there are some successful reports on the inactivated SIV vaccines (Scott E. J. Nature 253, 393 (1991); Le Grand R. et al., Nature 355, 684 (1992); Crange M. P. et al., Nature 355, 685-686 (1992); Arthur L. O. et al., J Virol 69, 3117-3124 (1195); Neidrig M. et al., Vaccine 11, 67-74 (1993)), it is not considered useful as a safe and effective AIDS vaccine because suspicion has been raised that the successful immunization resulted from action by xeno-antigen which the cultivated host cells harbor.

The live attenuated vaccines are prepared by partial deletion in the HIV genome, such as deletion of nef gene or nef and vpr genes (Descrosiers R. C. AIDS Res Hum Retroviruses 8, 411-421 (1992); Gibbs J. S. et al., AIDS Res Hum Retroviruses 10, 607-616 (1994); Cranage M. P. et al., Virology 229, 143-154 (1997); Wyand M. S. et al. Nature Med 3, 32-36 (1997)). However, such vaccines can regain the deleted genes in vaccinated animals, allowing them to be infectious. Accordingly, the live attenuated vaccines may not be completely safe because they can cause AIDS in vaccinated individuals (or animals).

The live recombinant vaccines are vectors in which non-essential genes of non-pathogenic viruses are replaced with genes coding HIV immunogens. There was disclosed an expression of gag, pol or env gene and an expression of an immunogenic region including V3 loop of HIV as a chimeric form in vaccinia virus, poxvirus, canary pox virus, avipox virus and poliovirus, or influenza virus (Tartaglia J. et al., Virology, 188, 217-232 (1992); Abimiku A. et al., Nature Med, 1, 321-329 (1995); Natuk R. J. et al., AIDS Hum Retroviruses 9, 395-404 (1993); Li S. et al., J Virol, 67, 6659-6666 (1993); Muster T. et al., J Virol 69, 6678-6686 (1995)). As this technology, in general, uses a part of the protein as a vaccine material, it cannot provide an efficient immunogen. In addition, the live recombinant vectors are unstable (Morrow, C. D. et al., AIDS Res Hum Retroviruses, 10, S61-S66 (1994); Anderson M. J. et al., AIDS Res Hum Retroviruses, 13, 53-62 (1997)).

The subunit vaccines are subunits of proteins encoded by HIV, which are naturally isolated or expressed by recombinant DNA technology. These vaccines can be easily manufactured, but they have a different conformation from original proteins existing in viral particles. Recombinant Env glycoproteins, gp120 and gp160, were expressed using mammalian and insect cell expression systems (Lasky, L. A., et al., Science, 249, 932-935 (1986); Barr, P. J. et al., Vaccine 5, 90-101 (1987); Hu, S-L. et al., J Virol 61, 3617-3620 (1987); Rusche, J. R. et al., Proc. Natl. Acad. Sci., 84, 6924-6928 (1987); Berman, P. W., et al. J Virol 63, 3489-3498 (1989); Ivey-Hoyle, M., and Rosenberg, M., Mol. Cell. Biol., 10, 6152-6159 (1990); Lasky, L. A. et al., Cell, 50, 975-985 (1987)). Upon being injected into chimpanzees, gp120 subunit vaccine expressed in the CHO cells could not confer protection against a viral challenge experiment (Berman, P. W. et al., Proc. Natl. Acad. Sci., 85, 5200-5204 (1988)).

Generally, vaccines of viral particle form are more immunogenic and stable than those of subunit form. There was recently developed a new technology in which the non-infectious virus-like particles (VLPs) that do not carry genetic materials were used as vaccines. For example, mutation in packaging genes can provide a VLP without an RNA genome, and a VLP containing unprocessed gag protein can be prepared using recombinant baculovirus or vaccinia virus (Gorelink R. J. et al., J Virol 64, 3207-3211 (1990); Gheysen D. E. et al., Cell 59, 103-112 (1989)). It was also reported that virus-like particles were produced from the cells co-transfected with two recombinant vaccinia viruses containing gagpol gene and env gene, respectively (Haffar O. K. et al., Virology; 183, 487-495 (1991)). Such pseudo-particles were effective for production of neutralizing antibodies, env-CD4 protecting antibodies, and syncytium inhibition, but they have the drawbacks in their not being mature virus particles and lack of infectivity.

As other forms of virus-like particles containing immunodeterminant of HIV, there were described hybrid particles including poliovirus capsovector, hepatitis B virus (HBV) core particles, HbsAg particles and yeast retrotransposon virus-like particles But, these hybrid particles contain only the partial region of the immunodeterminant of HIV, resulting in non-effective vaccines (Grene E. et al., AIDS Res Hum Retroviruses, 13, 41-51 (1997); Schlienger K., et al. J Virol 66, 2570-2576 (1991); Adams S. E. et al., Nature 329, 68-70 (1987); Layton G. T. et al., J Immunol, 151, 1097-1107 (1993); Eckart L. et al., J Gen Virol 77, 2001-2008 (1996)).

The inventors of the present invention attempted to develop a novel AIDS vaccine with mature virus-like particles using an alphavirus vector system. The inventors believe the virus-like particles will provide the way to prevent AIDS.

DISCLOSURE OF THE INVENTION

It is an object of the present invention to provide an expression vector expressing Gag protein, an expression vector expressing Env protein of HIV, an expression vector simultaneously expressing Gag and Env proteins of HIV, an expression vector expressing Gagpol polyprotein of HIV, and an expression vector simultaneously expressing Gagpol polyprotein and Env protein of HIV.

It is another object of the present invention to provide transformants transformed with the above expression vector.

It is a further object of the present invention to provide HIV-like particles (HIVLPs), a preparation method thereof, and use thereof, in which the above expression vector or its RNA transcript is introduced into animal cells.

It is still a further object of the present invention to provide a method of detecting HIV using a mature HIV-like particle and its application in diagnosis of HIV infections.

It is a yet further object of the present invention to provide a vaccine composition comprising the mature HIV-like particles, and also provide an AIDS vaccine composition comprising the expression vector or its RNA transcript.

It is a still further object of the present invention to provide a method of detecting the existence of antibodies specific for HIV antigens in a test sample, comprising the steps of: (a) collecting a test sample which may contain specific antibodies against HIV; (b) reacting the test sample with the mature HIV-like particle prepared according to the method of claim 21 under a condition which allows the antigen-antibody immune complex formation; and (c) detecting antigen-antibody complexes.

BRIEF DESCRIPTION OF THE DRAWINGS

FIG. 1 is a brief view showing a genome structure of HIV-1;

FIG. 2 is a restriction map showing structures of expression vectors pSFV and pSFV-helper;

FIG. 3 is a schematic diagram showing a process for construction of an expression vector pSFV/gag;

FIG. 4 is a schematic diagram showing a process for construction of an expression vector pSFV/gagpro;

FIG. 5 is a photograph showing western blotting of HIV-like particles with an AIDS patient serum, where the HIV-like particles were produced in BHK-21 cells transfected with pSFV-helper and pSFV/gag, or pSFV-helper and pSFV/gag-pro, and RNA transcript of pSFV/gagpro;

FIG. 6 is a photograph showing western blotting of HIV-like particles with an AIDS patient serum, where the HIV-like particles were produced in infected BHK-21 cells with in vitro activated HIV-like particles, prepared from BHK-21 cells transfected with pSFV-helper and pSFV/gag, or pSFV-helper and pSFV/gagpro, and RNA transcript of pSFV/gag-pro;

FIG. 7 is a photograph showing a result of immunocytochemistry for Gag protein in BHK-21 cells transfected with pSFV/gag or pSFV/gagpro vector, staining with anti-p24 polyclonal antibody;

FIG. 8 is a photograph showing an electro-microscopically observed result for negative-staining of VLPs, isolated from supernatant from a cultivated medium of BHK-21 cells transfected with pSFV/gag vector (A) or pSFV/gagpro RNA transcript (B)(X140,000);

FIG. 9 is a schematic diagram showing a process for construction of a pSFV/env expression vector;

FIG. 10 is a photograph showing a result of immunocytochemistry for Gag protein in BHK-21 cells transfected with pSFV/env RNA transcript and pSFV-helper RNA transcript, staining with anti-gp160 monoclonal antibody;

FIG. 11 is a photograph showing western blotting of cell lysates of BHK-21, infected with in vitro activated defective SFV particles, with an AIDS patient serum, where the defective SFV particles prepared from BHK-21 cells transfected with pSFV/env RNA transcript and pSFV-helper RNA transcript;

FIG. 12 is a photograph showing a result of immunocytochemistry for Gag and Env proteins of HIV-1 in BHK-21 cells co-transfected with pSFV/gag and pSFV/env RNA transcript, staining with anti-gp160 monoclonal antibody (B) or with an AIDS patient serum (C);

FIG. 13 is a photograph showing agarose gel electrophoresis pattern for RT-PCR and PCR products of RNA genome packaged in VLPs, which produced in BHK-21 cells transfected with pSFV/gag RNA transcript, or with pSFV/gag and pSFV/env RNA transcript;

FIG. 14 is a photograph for western blotting showing production of VLPs composed of Gag and Env in infected BHK-21 cells with in vitro activated defective SFV particles, prepared in BHK-21 cells co-transfected with pSFV-helper and pSFV/gag RNA transcript, or with pSFV/helper and pSFV/env RNA transcript;

FIG. 15 is a schematic diagram showing a process for construction of an expression vector pSFV/pro;

FIG. 16 is a schematic diagram showing a process for construction of an expression vector pSFV/env-gag;

FIG. 17 is a schematic digram showing a process for construction of an expression vector pSFV/env-gag-pro;

BEST MODE FOR CARRYING OUT THE INVENTION

The present invention provides alphavirus-based expression vectors expressing structural proteins of HIV. The terms "HIV" used in the present invention includes all kinds of human retrovirus such as HIV-1, HIV-2, HTLV-1, and HTLV-2.

The terms "Alphaviruses" used in the present invention includes virus species which are categorized into alphavirus and their subtypes in the field of biotechnology and virology such as Estern Equine Encephalitis virus (EEE), Venezuelan Equine Encephalitis virus (VEE), Everglades virus Mucambo virus, Pixuna virus, Western Encephalitis virus (WEE), Sinbis virus, South African Arbovirus No. 86, Girdwood S. A. virus, Ockelbo virus, Semliki Forest virus, Middleburg virus, Chikungunya virus, O'Nyong-Nyong virus, Ross River virus, Barmah Forest virus, Mayaro virus, Getah virus, Sagiyama virus, Bebaru virus, Mayaro virus, Una virus, Aura virus, Whataroa virus, Babanki virus, Kyaylagach virus, Highlands J virus, Fort Morgan virus, Ndumu virus, Buggy Creek virus and other viruses which have been categorized into alphaviruses by the International Committee on Taxonomy of Viruses.

Alphaviruses, which belong to the Togaviridae family, are enveloped positive-strand RNA viruses with a broad range of susceptible cells including insects, birds, and mammalian animals. An alphavirus RNA genome is itself infectious and encodes RNA replicase, allowing alphavirus to be used as an expression vector capable of performing RNA replication and translation (Liljestrom, P. and Graoff, Biotechnology, 9, 1356-1361 (1991)).

It is preferable that Alphavirus is selected from "Semliki Forest virus" (SFV) and "Sindbis virus", and most preferable. Alphavirus is selected from Semliki Forest virus (SFV). An SFV-based expression vector, pSFV, provided in an embodiment of the present invention, is prepared from insertion of a SFV cDNA genome into a plasmid harboring SP6 promoter, providing in vitro translation using SP6 polymerase and expression of foreign genes inserted instead of structural genes, under the control of 26S subgenomic promoter.

Figure 1:
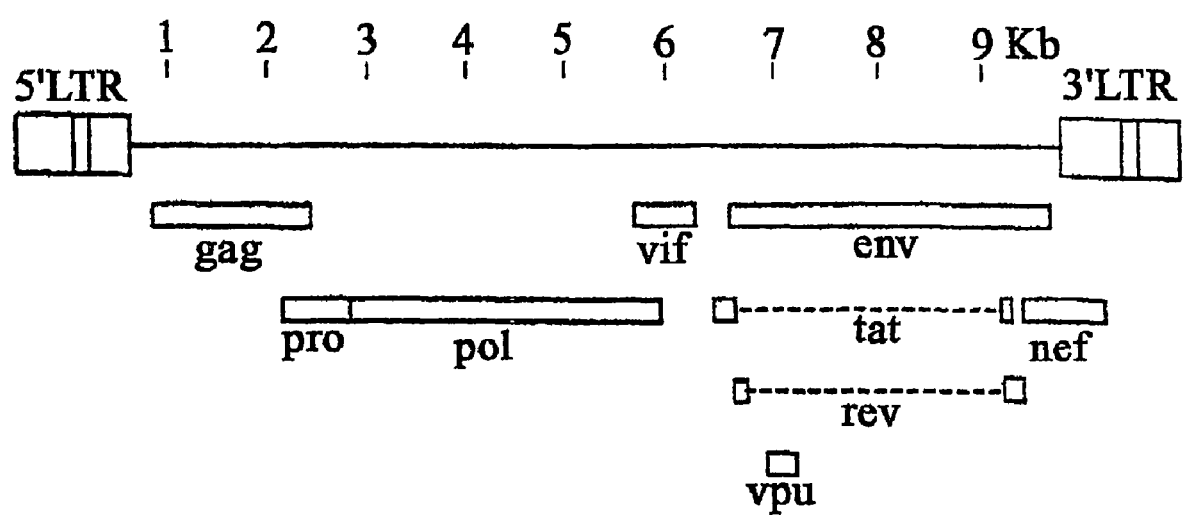
Figure 2:
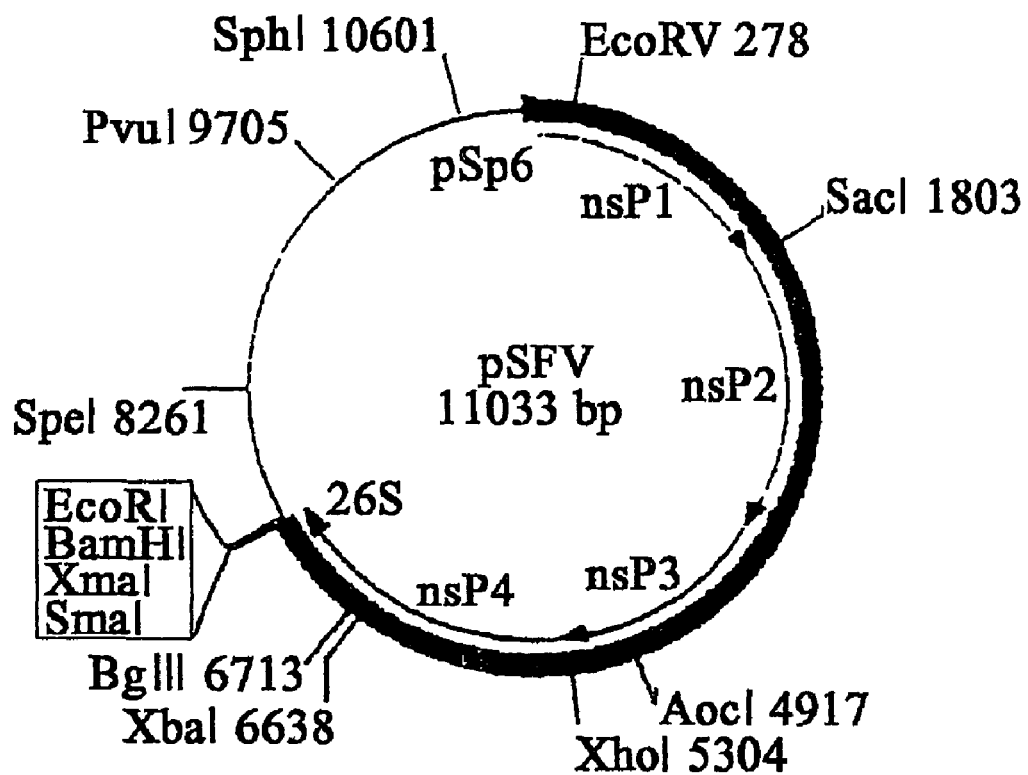
Figure 2:
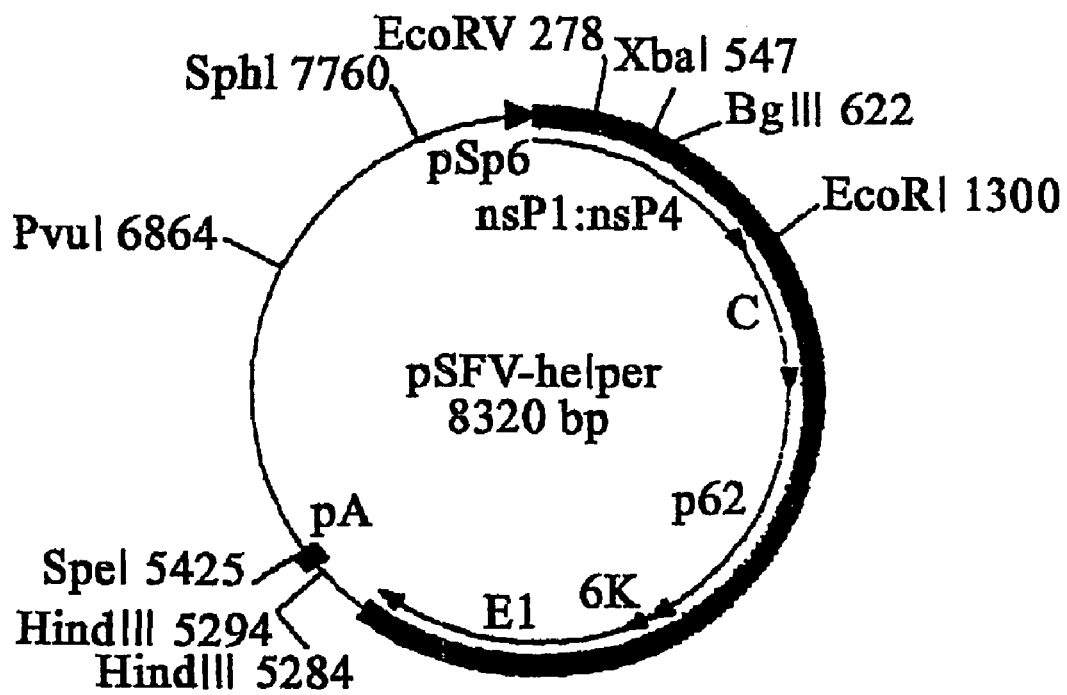

An in vivo packing system is necessary for introduction of recombinant RNA into cells by injection. A pSFV-helper vector contains a RNA replication signal of SFV and genetic information to express structural genes, but it lacks a packaging signal for genomic RNA. Accordingly, when the pSFV vector is co-transfected with the pSFV-helper, there can be viral particles produced which carry only recombinant RNA inside of SFV structure proteins. Upon infecting susceptible cells, the viral particles express recombinant genes, but cannot reconstitute viral particles. With reference to FIG. 2, there is illustrated the structures of pSFV and pSFV-helper vectors used in an embodiment of the present invention. All DNA vectors and their RNA transcripts utilized in the present invention are within the range of the present invention.

In an aspect of the present invention, there are provided alphavirus-based expression vectors carrying gag, gagpro, gagpol and env gene, respectively, an expression vector carrying env-gag genes, an expression vector carrying env-gag-pro genes, an expression vector carrying env-gag-gagpro genes, an expression vector carrying env-gag-gagΔpro genes and an expression vector carrying gagpol-env genes, where each gene of HIV is regulated under the alphavirus subgenomic promoter by separately inserting the genes into the downstream of 26S subgenomic promoter. It is known that expression of Pro synthesis is dependent on the amount of Gag protein (Velissarios K. et al., Virology, 193, 661-672 (1993); Magdeleine H. et al., J Virol. 72, 4819-4824 (1998); Joel G. et al., Virology, 244, 87-96 (1998)). To achieve maximum expression of Pro protein through processing of Gag protein, there were constructed expression vectors characterized in the gagΔpro gene, in which nucleotides responsible for ribosomal frameshifting are deleted at the junction between gag and pro genes, or gagpro gene was linked to 26S promoter, respectively, in addition that env gene located at the downstream of gagpol gene was linked to 26S promoter.

The present invention provides an alphavirus-based expression vector in which gag gene of HIV-1 is operably linked to a promoter. As used herein, the term "operably linked" means that the DNA sequences being linked are typically contiguous and in reading frame. In an embodiment of the present invention, a pSFV/gag vector is described (refer to Example 1). The present invention provides an alphavirus-based expression vector in which gagpro gene is operably linked to a promoter. A pSFV/gagpro vector is exemplified in an embodiment of the present invention (refer to Example 1). Also, the present invention provides an alphavirus-based expression vector in which an HIV-1 env gene is operably linked to a promoter. A pSFV/env vector to exemplified in an embodiment of the present invention (refer to Example 4).

The present invention provides an alphavirus-based vector simultaneously expressing HIV-1 env and gag. More preferably, the present invention provides an alphavirus-based expression vector comprising the nucleotide sequence of HIV env, operable linked to a first subgenomic promoter, and the nucleotide sequence of HIV gag, operably linked to the second subgenomic promoter. In an embodiment of the present invention, plasmid pSFV/env-gag is exemplified (refer to Example 9). Also, the present invention provides an alphavirus-based vector comprising the nucleotide sequence of HIV pro, operably linked to a promoter. In an embodiment of the present invention, plasmid pSFV/pro is exemplified (refer to Example 9).

In a further aspect of the present invention, there is provided an alphavirus vector simultaneously expressing env, gag and pro genes of HIV-1. More preferably, the present invention provides an alphavirus-based expression vector comprising env, gag and pro genes were operably linked to a first, second and third subgenomic promoter, respectively. The vector pSFV/env-gag-pro is exemplified (refer to Example 9).

The present invention provides an alphavirus vector expressing a gagpro gene of HIV-1 and a gene encoding constitutive transport element (CTE), and more preferably an alphavirus-based expression vector comprising a gagpro gene operably linked to a promoter in addition to a gene encoding CTE. The vector pSFV/pagpro-CTE is exemplified (refer to Example 9).

Also, the present invention provides an alphavirus vector expressing env, gag, gagpro genes of HIV-1 and a gene encoding CTE, and more preferably an alphavirus-based expression vector comprising env, gag and gagpro genes operably linked to a first, second and third subgenomic promoter, respectively, in addition to a gene encoding CTE. The vector pSFV/eng-gag-gagpro-CTE is exemplified (refer to Example 12).

The present invention provides an alphavirus vector expressing env, gag, and gagΔpro genes of HIV-1 and a gene encoding CTE, and more preferably an alphavirus-based expression vector comprising env, gag and gagΔpro genes operably linked to a first, second and third subgenomic promoter, respectively, in addition to a gene encoding CTE. Herein, it should be noted that the gagΔpro means a gagpro gene prepared from deletion of nucleotide sequence at the junctional region between gag and pro genes, providing an open reading frame and allowing expression of pro protein without frame-shift translation at 3' end of gag mRNA. Exemplified is pSFV/env-gag-gagΔpro-CTE vector (refer to Example 13).

The present invention provides an alphavirus vector expressing a full-length gagpro gene of HIV-1, and more preferably an alphavirus-based expression vector comprising a full-length gagpro gene operably linked to a downstream of a subgenomic promoter, with an embodiment of pSFV/gag-pol vector (refer to Example 14).

The present invention provides an alphavirus vector simultaneously expressing env and gag genes of HIV-1, and more preferably an alphavirus-based expression vector comprising env and gag genes operably linked to a first and second subgenomic promoter, respectively, in addition to a gene encoding MCTE Exemplified is pSFV/gag-envMCTE vector (refer to Example 16).

The present invention provides an alphavirus vector simultaneously expressing gagpol and env genes of HIV-1, and more preferably an alphavirus-based expressing vector comprising gagpol and env genes operably linked to a first and second subgenomic promoter, respectively, in addition to a gene encoding MCTE. Exemplified is pSFV/gagpol-envMCTE vector (refer to Example 16).

The expression vectors of the present invention can be prepared, with some modification, using recombinant DNA technology known in the field to which the present invention belongs.

The present invention provides a method of preparing HIV-1 structural proteins including Gag, Pro and/or Env in the form or precursors or processed subunits with the use of alphavirus-based expression vectors which are described above. The alphavirus-based expression vectors of the present invention can express proteins in a wide range of host cells. In addition, the present invention provides a method of preparing Gag, Pro and/or Env proteins of HIV-1 by expressing the expression vectors or their RNA transcripts in host cells, and more preferably, in animal cells. It is preferable that the animal cells are prepared from birds, mammalians, reptiles, amphibians, insects and fishes (aquatic animals), and examples of mammalians include humans, monkeys, hamsters, rats (or mice), and pigs. Most preferably, an expression system consisting of a host cell and a vector is BHK-21 cells/pSFV vector or COS cells/pSFV vector, but the expression system of the present invention is not limited to them.

The alphavirus expression vectors and their RNA transcripts can be introduced into animal cells, such as BHK-21 cells, by a conventional transfection method including DEAE dextran mediated transfection, calcium-phosphate co-precipitation, and more preferably, electroporation. In an embodiment of the present invention, RNA transcript of pSFV vector was efficiently transfected into a host cell by electroporation. Also, the above transfection methods can be used for co-transfection.

Expression of foreign genes in animal cells can be maximized by the introduction of infectious viral particles. Regarding this, the present invention provides a method of preparing the above proteins of HIV, comprising an infection of host cells with an infectious viral particle harboring RNA transcripts, which is generated using a helper virus. In Examples 2 and 6, the method is exemplified HIV-1 proteins, produced by infecting host cells with defective viral particles generated with the use of a helper virus or RNA transcripts of the expression vectors of the present invention, can be isolated using conventional methods, including ion-exchange chromatography, affinity chromatography, and gel infiltration chromatography.

In addition, the present invention provides host cells transiently transformed with RNA transcripts of the expression vectors of the present invention and VLP harboring recombinant RNA, and also provides host cells permanently transformed with the expression vectors. The permanently transformed cells can be provided as an animal cell line having a cytomegalovirus (CMV) promoter necessary for integration of cDNA of HIV genome into chromosome of host cells, a gene encoding constitutive transport element (CTE) for reverse transcriptase-independent expression, and an antineomycin gene as a selective marker. The CTE gene, more preferably, is a gene encoding MPMV (Mason-Pfizer monkey virus).

The present invention provides a method of preparing an infectious HIVLP using the expression vectors and the host cells described above, and more particularly, a method of preparing a Gag-containing immature HIVLP by introducing an expression vector expressing Gag protein into host cells. When Gag is not processed by protease, mature viral particles are not generated, resulting in immature virus-like particles (VLPs). "Virus-like particle (VLP)" means a virus particle, which is not identical to wild-type (mature) viral particles, but has similar physicochemical properties to wild types. An "Immature virus-like particle (immature VLP)" is a viral particle showing the morphology characteristic of viral particles while it is unable to complete the processing necessary for production of wild virions. "Replicon" means a self-replicating RNA containing indispensable genes for gene replication and is thus capable of being used as an expression vector for expression of foreign genes while virus proliferates by combination to foreign genes.

HIV with only Gag protein is capable of producing immature viral particles without infectivity. Also, it is known that neutralizing antibodies against HIV mainly bind to epitopes located at an envelope (Env) protein that has a variable amino acid sequence. Thus, the Env protein is a main target for development of HIV vaccines, with growing concerns for the development of a Gag-containing recombinant viral particle carrying Env protein. To obtain such a HIV vaccine, the present invention provides a method of preparing an immature HIVLP composed of Gag and Env proteins by simultaneously expressing the two proteins in host cells, which co-transfected with expression vectors harboring gag and env genes.

On the other hand, the co-transfection method used for the production of HIVLP requires many steps and is not effective. To overcome these problems, the inventors of the present invention used a recombinant plasmid carrying 2 or 3 target genes, offering an economic and effective method in preparing and recovering HIVLP. Accordingly, the present invention provides a method of producing an immature HIVLP composed of Gag and env proteins, supplied by inserting each of gag and env genes into the downstream of each promoter of alphavirus replicon and introducing the resulting replicon vector into host cells.

During an assembly or budding process, or in a viral particle, gag protein is cleaved by protease, and the cleaved subunit proteins assemble, producing mature particles. The HIVLP composed of only gag protein varies greatly in size and morphology from a natural HIVLP. Also, unless a HIVLP composed of Gag and Env undergoes the processing by protease, mature viral particles cannot be produced. To induce an effective immune response, it is important to provide similar immunogens (antigens) to a wild type HIV. Accordingly, production of mature HIVLP is a strong tool for preparation of a HIV vaccine. In the present invention, the inventors developed a method of producing a mature HIVLP through the simultaneous expressions of Gag and Pro proteins, or Gag, Env and Pro proteins. The "mature virus-like particle (mature VLP)" referred to (defined) as the HIVLP that has structural proteins completely processed by protease (Pro) and shows similar morphology and size to a wild type HIV. In the present invention, it was found that a great deal of mature HIVLP was produced when gagpol and env genes were simultaneously expressed.

The HIV-like particle (HIVLP) is considered to be a most preferable form for HIV vaccines or for antigens for diagnosing of HIV infections. However, expression of Gag, Env, and/or protease in each different vector to produce HIVLP is complex and ineffective, in addition that it is very difficult to establish a stable cell line producing HIVLP. In the present invention, there was successfully developed an alphavirus-based expression vector simultaneously expressing Gag, Env and protease at amounts large enough to produce HIVLP, as well as successfully prepared and isolated an infectious HIVLP.

The present invention further provides a method of preparing enough amount of the above expression vectors for induction of immune response, a vaccine composition including RNA transcripts of the expression vectors or the HIVLP, and a method of preventing or treating AIDS comprising administration of the vaccine composition. Preferably, the HIVLP is mature HIVLP, immature HIVLP, infectious HIVLP or non-infectious HIVLP, and most preferably, mature HIVLP. Due to its three dimensional structure, HIVLP, when it used as a vaccine, induces excellent immune response.

The vaccine composition of the present invention can be administered to human in a type suitable to living bodies. The type suitable to living bodies refers to a type of material capable of being administered to living bodies with a higher effect of treatment or prevention than its toxic effect. The materials can be administered to animals, and more preferably to humans.

The vaccine of the present invention may additionally include a suitable diluent, excipient and/or carrier. The excipient includes a suitable adjuvant capable of improving immunogenicity of the vaccine. The adjuvant can be selected from the group consisting of endotoxin lipid-A of Gram (–) bacteria, trehalos dimycholate of *Mycobacterium* species, phospholipid lysolecitin, dimethyldioctadecylammonium bromide (DDA), a polyoxypropylene-polyoxyethylene (POP-POE) block copolymer, aluminum hydroxide, and liposome. The carrier may be anything unless there are induced unwanted antibodies in administered individuals. Especially, various suitable carriers or diluents such as saline, buffered saline, and a mixture of saline and non-specific serum albumin may be used for the present invention. The pharmaceutical composition may include a vehicle, a buffer, an anti-oxidant, carbohydrate such as glucose, sucrose or dextrin and a chelating agent such as EDTA, and additionally include water, saline, glycerol, ethanol, an emulsifier, a moistening agent, or a pH adjusting agent.

The vaccine composition may include an adjuvant capable of enhancing immune response. Examples of the adjuvant include aluminum hydroxide (alum), thr-MDP, nor-MDP, and MPT-PE. Also, the vaccine may include cytokine such as GM-CSF, IL-2, IL-12, TNF and IFN, which are known to enhance the immune response.

The dosage of vaccine may be dependent on factors such as health condition, age, sex, body weight and immune response capability of vaccine. Also, the dosage may vary in order to achieve the maximal response. For example, the vaccine may be administrated at a same amount every day, or the dosage may be gradually reduced in an emergency. The vaccine may be administered subcutaneously, intravenously, intramuscularly, orally, or intradermally as usual. The inhalation or suppository administration can be applied. The booster administration can be given after 4 to 6 weeks.

The present invention provides a diagnostic kit for HIV infection and a diagnostic method using thereof. The diagnostic kit comprises the steps of: (a) reacting HIVLP with a biological sample from an animal, especially human; and (b) detecting binding of an antibody in the sample to the HIVLP. Also, there is provided a method of diagnosis of HIV infection using the diagnostic kit. Methods to measure the binding degree between antigen and antibody are well known in the field to which the present invention belongs. ELISA (enzyme-linked immunosorbant assay) is one of the applicable methods. The antigen-antibody binding in the diagnosis can be performed directly or competitively.

From the viewpoints above, the present invention provides a method of detection antibodies specific against HIV antigen in the test sample, comprising the steps of: (a) collecting a test sample suspected to contain a antibodies specific against HIV; (b) reacting the test sample with the mature HIV-like particles prepared according to the method described in example 18 under a condition which allows antigen-antibody immune complex to form in the sample; and (c) detecting the antigen-antibody complexes formed in the test sample.

The mature HIV-like particles of the present invention, as an antigen, can be useful for performing immunoassay including ELISA, RIA and other non-enzymatically linked antibody tests, or for detecting retrovirus antigens (e.g. HIV antigen) and anti-retrovirus antibodies (e.g. anti-HIV antibody). The mature HIV-like particles, in ELISA, can be attached onto a specific surface, such as a well of polystyrene microtitration plates, where proteins can bind. The plates are washed to remove the unbound mature HIV-like particles. After removing incompletely attached mature HIV-like particles by washing, the plate is blocked with a non-specific protein such as bovine serum albumin (BSA) or casein, reducing non-specific binding of the mature HIVLP to the surface.

Thereafter, clinical or biological samples may be applied on the fixed surface, allowing immune complex (antigen-antibody complex) formation. Herein, the sample may be diluted with a diluent such as BSA, bovine gammaglobulin (BGG), or a phosphate buffered solution (PBS)/Tween solution, followed by incubation at 25° C. and subsequently at 37° C. for 2 to 4 hours. Non-immune complexes are then removed from the surface by washing. The washing can be performed by PBS/Tween or boric acid buffered solutions.

After washing, a qualitative of qualitatitve test could be performed by adding a specific secondary antibody to a first antibody, which formed an immune complex with the mature HIVLP. In the case of that the sample comes from humans, a secondary antibody is specific against mainly IgG among human immunoglobulins. To easily detect the immune complex, a secondary antibody is conjugated with an enzyme capable of using a chromogenic substrate, thus allowing qualitative analysis using a spectrophotometer.

To identify multiple antibodies reacting with multiple HIV isolates, multiple HIV-like particles, immunologically different, could be attached to a specific surface. To detect an anti-HIV antibody recognizing a conserved epitope among HIV isolates, one or a limited number of mature HIVLP could be attached. To identify antibodies reacting with one HIV isolate (e.g. LA1, MN, SF2 or HXB2), one mature HIVLP specific to the HIV isolate of the present invention could be attached. This additional diagnostic system can be applied for detection of a specific HIV isolate in clinical tests and medical or medical law fields.

In addition, another diagnostic method could be necessary to identify immunologically different HIV isolates, which belong to different classification. Examples of the immunologically different HIV isolates include LA1, MN, SF2, HXB2 and primary HIV-1 isolates. In an aspect of this diagnostic method, the mature HIVLP of the present invention could be useful for production of antibodies including monoclonal antibodies capable of specifically recognizing the immunologically different HIV isolates. It is possible that the mature HIVLP of the present invention, which is immunologically different, may be used as a vaccine and a diagnostic immunogen. A mixture combining mature HIVLPs could be provided for protection and/or diagnosis of mixed-isolates. In this case, the mixture of immunogens may be called a "cocktail".

A composition having immunogenic properties of the present invention, in the non-mixed or cocktail form, can be used for detecting HIV antigen(s) in a sample including a biological sample, or for producing a HIV-specific antibody (including monoclonal antibody) to neutralize HIV.

In a further diagnostic application, the mature HIVLP of the present invention can be used for stimulating HIV-specific T-cells in biological samples obtained from HIV-infected patients with an aim for diagnosis and therapy.

The present invention will be explained in more detail with reference to the following examples in conjunction with the accompanying drawings. However, the following examples are provided only to illustrate the present invention, and the present invention is not limited to them.

EXAMPLE 1

Construction of Expression Vectors, pSFV/gag and pSFV/gagpro

Figure 3:
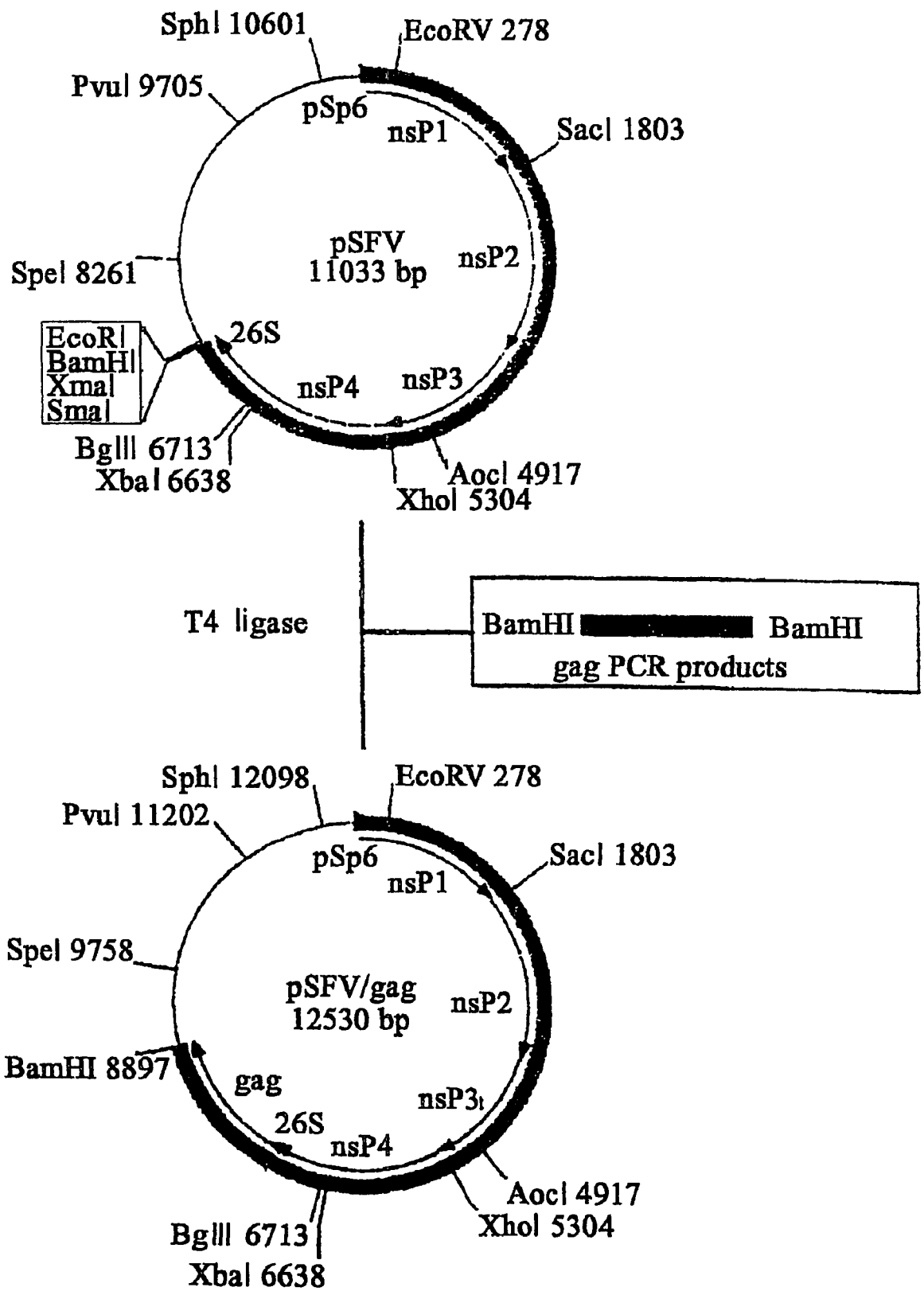
Figure 4:
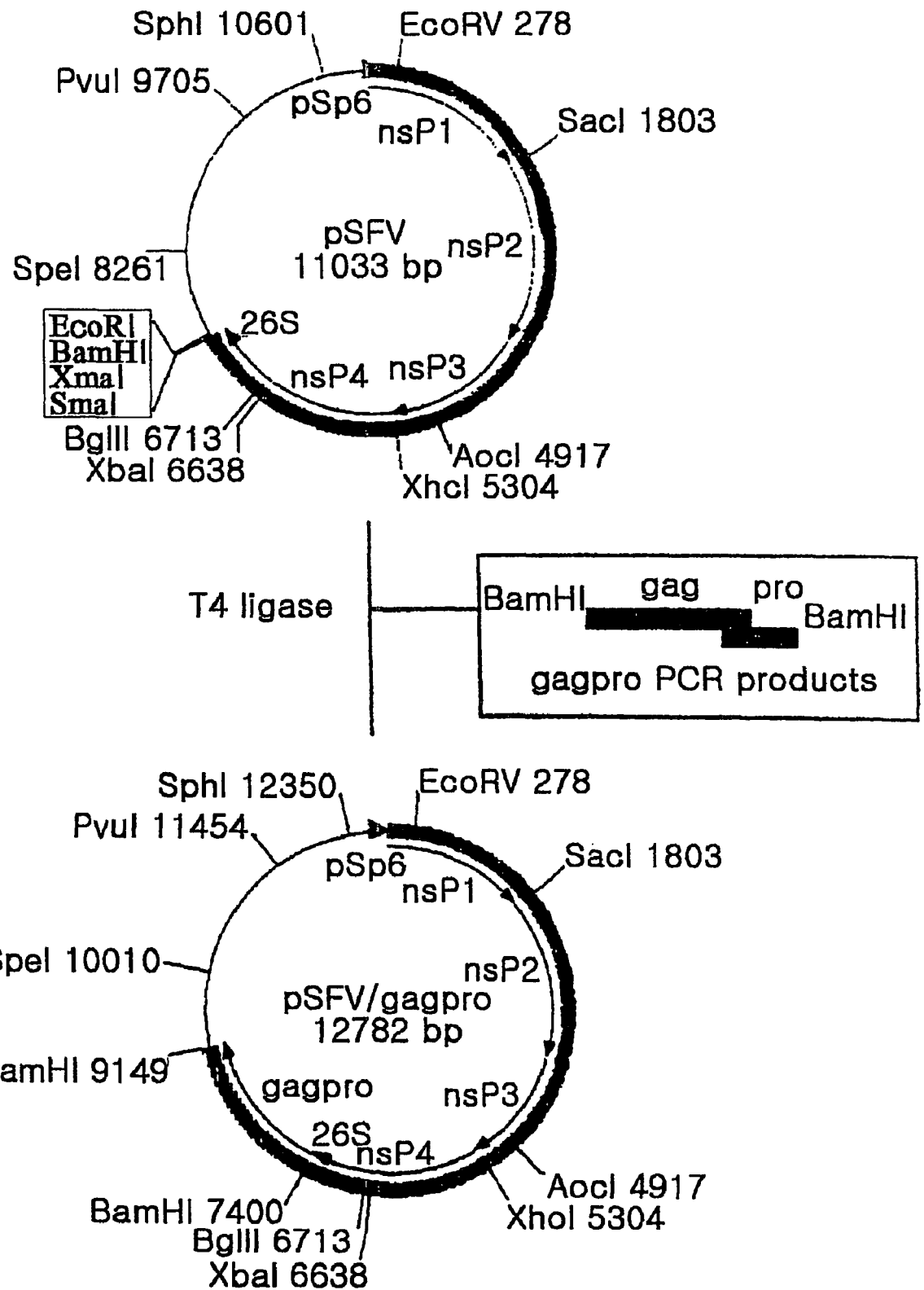

Gag protein of HIV and its proteolytic cleavage products are the major structural components of the virion, and Gag itself is sufficient to direct assembly and release of virus-like particles without any other viral proteins. Gag protein is cleaved by viral protease (PR) encoded by pol gene, generating matrix (MA, p17), capsid (CA, p24), nucleocapsid (NA, p9), and p6, which are assembled to produce mature viral particles (Gheysen D. et al, Cell, 59, 103-112 (1989)). Therefore, in this study, there was constructed an expression vector capable of expressing Gag by inserting a gag gene into a replicon, as follows. To amplify full-length a gage gene, PCR was performed with a primer set consisting of primers 1 and 2 below, using HIV clade E genome (Genbank accession No. U51188, Journal of Virologly, 1996), containing full-length gag gene (832 to 2328 bp), as a template. Also, to amplify a pro gene in addition to a gag gene, PCR was performed with primers 1 and 3, below, using HIV clade E genome, containing a gag gene, frame shift site and a pro gene (832 to 2577 bp), as a template. In the two cases, a PCR mixture was prepared as follows: plasmid pUHD (100 ng/µl) carrying full-length HIV-1 clade E genome, used as the template, was mixed with 4 µl of 2.5 mM dNTP (Boehringer Mannheim (BM), Germany), 1 µl of sense primer (100 pmol/µl), 1 µl of antisense primer (100 pmol/µl), 5 µl of 10×Taq polymerase buffer, 37 µl distilled water. The PCR mixture was pre-incubated at 98° C. for 5 min, and then supplemented with 1 µl of Taq polymerase, followed by a PCR reaction of 30 cycles in which each cycle was composed of 1 min at 94° C., 2 min at 55° C., and 3 min at 72° C. The amplified products for HIV-1 gag and gagpro were cloned into BamH1 site of pSFV vector, respectively, giving recombinant vectors, pSFV/gag (refer to FIG. 3) and pSFV/gagpro (refer to FIG. 4).

Primer 1: Sense (SEQ ID NO.: 1)
5'-GCGGATCCCGGGATGGGTGCGAGAGCGTCAATATTAAGT-3'

Primer 2: Antisense (SEQ ID NO.: 2)
5'-CGCGGATCCCTGTTACTGTGACAAGGGGTCGTTGCCAAA-3

Primer 3: antisense (SEQ ID NO.: 3)
5'-CGCGGATCCCTGCAGTTAAAGTACAACCAATCTGAGTCAACA-3'

EXAMPLE 2

Figure 5:
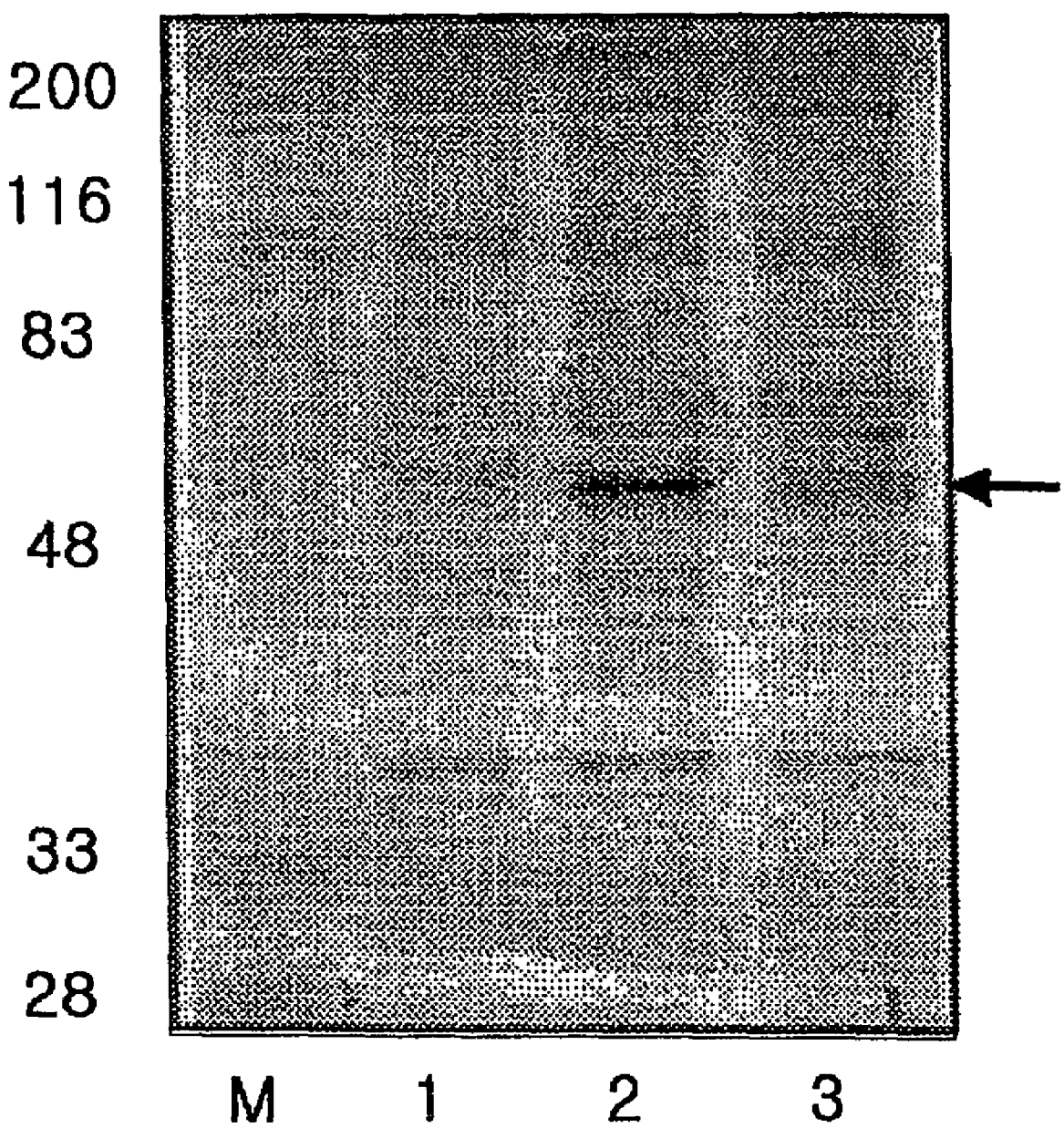
Figure 6:
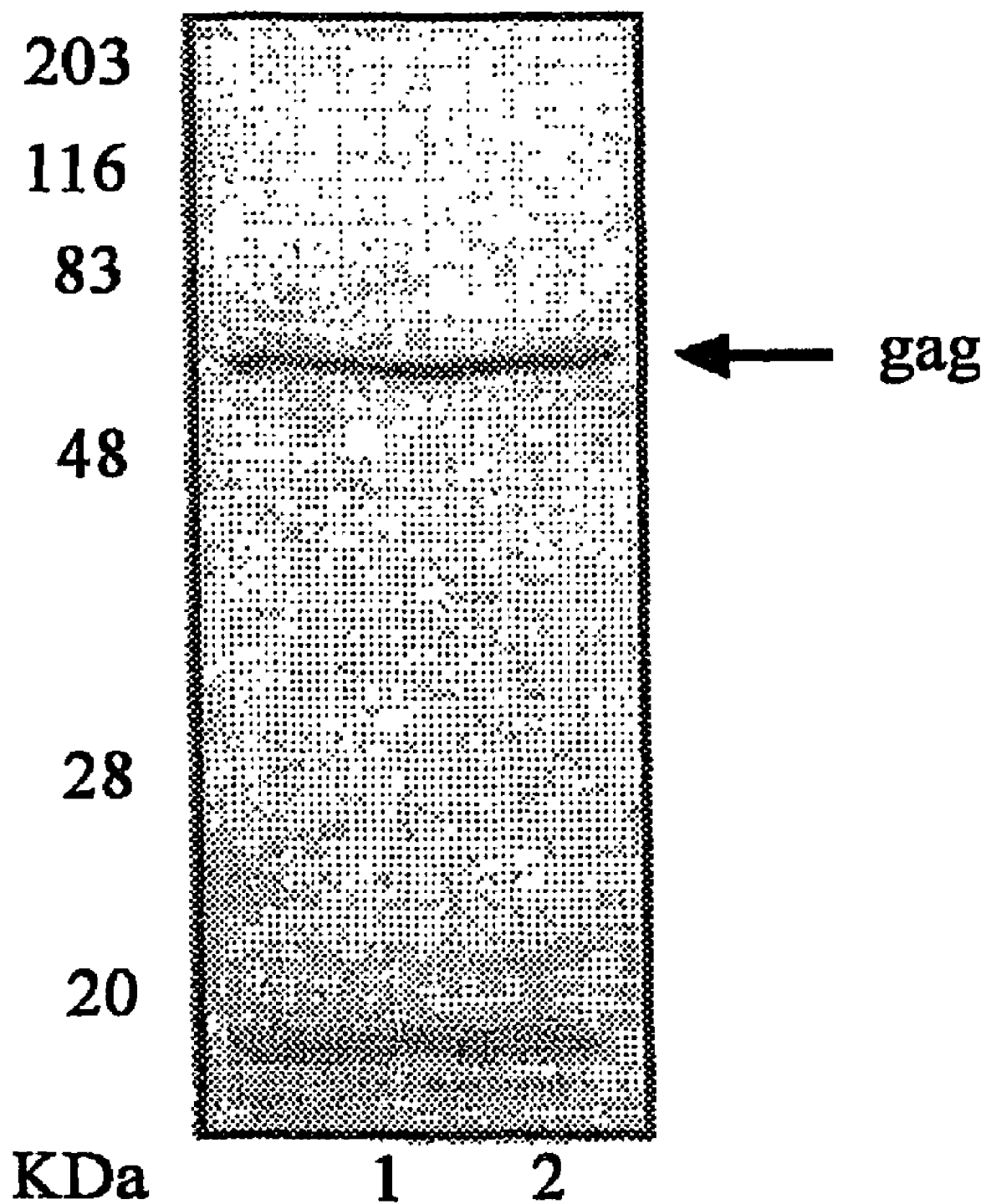

Production of VLP Using pSFV/Helper and pSFV/gag, or pSFV-Helper and pSFV/gagpro Protease (Pro) of HIV-1 was activated during or after the budding of virion, and was involved in the processing of structural polyproteins including Gag and Gagpol precursors. In this example, the recombinant vectors prepared in Example 1, pSFV/gag and pSFV/gagpro, were expressed with pSFV-helper in host cells.

pSFV/gag and pSFV/gagpro vectors were completely linearized with the use of a restriction enzyme pvuI, and purified by phenol/chloroform extraction. A reaction mixture was prepared from 10 μl of the plasmid 10 μl of DNA, 5 μl of 10×SP6 buffer (TaKaRa), 2.5 μl of 100 mM DTT, 5 μl of rNTP mix (10 mM ATP, 10 mM CTP, 10 mM UTP, 5 mM GTP, BM), 2 μl of Rnasin(BM), 1.5 μl of SP6 RNA polymerase (TaKaRa) and 19 μl distilled water, and then incubated at 37° C. for 1 hour 30 min. Transfection was then performed by electroporation, as follows: with 25 μl (1 μg) of pSFV-helper RNA transcripts, 50 μl of the resulting RNA transcript of gag or gagpro gene was added to 800 μl of BHK-21 cells ($10^7$ cells/ml) suspended in PBS (phosphate buffered saline, 1.37 mM Sodium Chloride, 0.02 mM Potassium Chloride, 0.1 mM Phosphate Buffer/ ml), and electroporation was then carried out at room temperature in a 0.4 cm electroporation cuvette using a Bio-Rad Gene Pulser, with two pulses of 830 V/25 μF. 48 hours after transfection, the cultivated medium was centrifuged at 3500 rpm for 15 min and the obtained supernatant was then ultra-centrifuged for 2 hr at 30,000 rpm at 4° C. using a Beckman SW41 rotor, giving a pellet containing viral particles. The pellet was resuspended in TNE buffer (50 mM Tris-HCl, pH 7.4, 100 mM NaCl, 0.5 mM EDTA) and stored at −70° C. The defective VLPs contained in the pellet were electrophoresed by a SDS-polyacrylamide gel, and were analyzed by Western blotting using serum from AIDS patients (refer to FIG. 5, lane M: negative control; lane 1: VLP produced from pSFV-helper and pSFV/lacZ; lane 2: VLP produced from pSFV-helper and pSFV/gag; lane 3: VLP produced from pSFV-helper and pSFV/gagpro). In lane 2 of FIG. 5, Gag protein was detected. This indicates that Gag protein was expressed in BHK-21 cells transfected with pSFV/gag RNA transcripts, and HIVLPs composed of Gag protein were released into culture medium with SFVLP. It was revealed that pSFV/gagpro, prepared for expressing Pro protein as well as Gag protein produced less Gag protein than pSFV/gag (refer to lane 3 of FIG. 5). BHK-21 cells were infected with the produced viral particles, as follows: to activate defective VLPs, 100 μl of suspension of defective VLPs in TNE buffer was incubated with 5 μl of chymotrypsin (10 mg/ml), 5 μl of 50 mM Cacl$_2$ for 30 min on ice, and 45 μl of Aprotinin (2 mg/ml, Sigma, USA) was then added to terminate the protease activity. The activated VLPs were added to monolayered BHK-21 cells with 70% confluency and then incubated for 90 min at 37° C. under 5% CO$_2$, allowing for infection of BHK-21 with the VLPs. Culture medium was then aspirated, and a new medium was refed and incubation was preceded for 48 hours. The BHK-21 cells were lysed with 200 μl of a lysis buffer (1% NL40, 50 mM Tris-HCl, pH 7.6, 150 mM NaCl, 2 mM EDTA, 1 μg, ml PMSF), and centrifuged at 12000 rpm for 5 min at 4° C. The supernatant was mixed with a sample buffer and then boiled for 5 min. The denatured samples were separated by SDS-PAGE (12% ). The separated proteins were transferred onto a PVDF membrane (BM) for 2 hrs under a condition of 15 V and 7 mA, and Western blotting was performed using specific antibodies, where serum from AIDS patients was used as a first antibody and biotinylated anti-human IgG as a second antibody. The membrane was then reacted with an avidin-biotin solution and the color was developed with DAB solution (refer to FIG. 6, lane 1: BHK-21 cells infected with VLP from pSFV/gag; lane 2: BHK-21 cells infected with VLP from pSFV/gagpro). As a result of reinfection, the band of 55 kDa presented that Gag proteins were produced in cytoplasm of BHK-21 cells. Therefore, these results suggest that VLP obtained from pSFV/gag or pSFV/gagpro contains a gag gene and is infectious.

EXAMPLE 3

Production of VLP using pSFV/gag or pSFV/gagpro Expression Vectors

Figure 7:
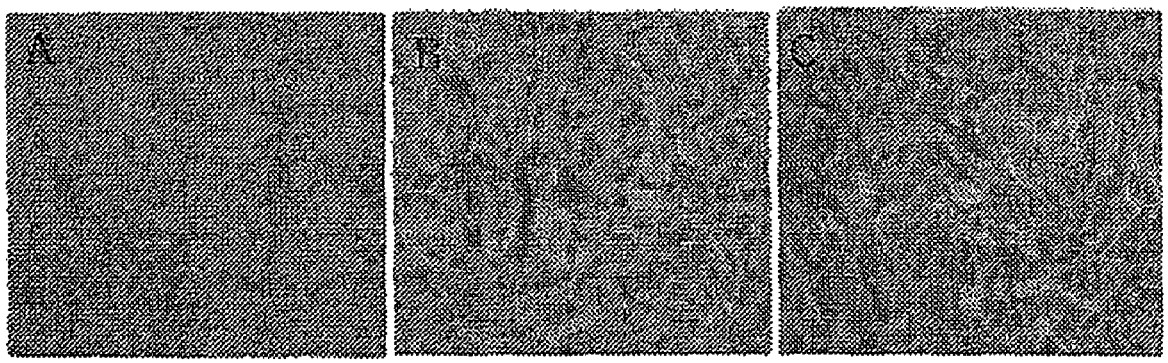
Figure 8:
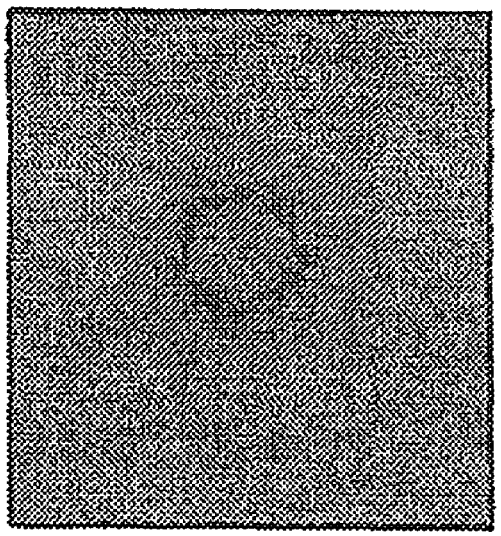
Figure 8:
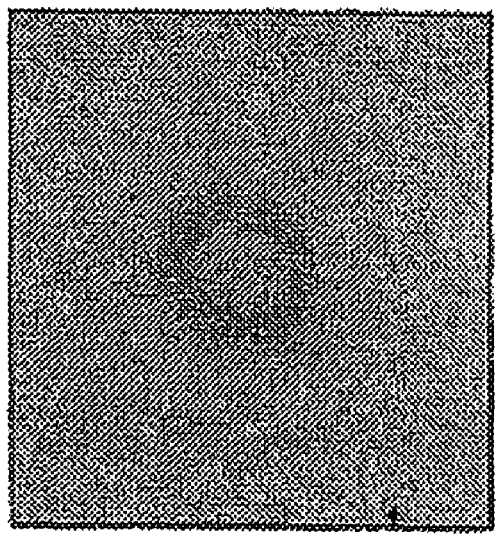

VLPs prepared in Example 2 are a mixture of VLP composed of a core of SFV (SFVLPgag or SFVLPgagpro) and VLP composed of a core of HIV-1 (HIVLPgag or SEVLP-gagpro). To obtain only VLPs composed of a core of HIV-1, pSFV/gag and pSFV/gagpro prepared in Example 1 were transcribed in vitro and transfected into BHK-21 cells without pSFV-helper RNA transcripts according to the method of the above Example 2. The transfected cells were fixed with cold absolute methanol, cooled at −20° C., for 4 to 6 min, blocked with 1% gelatine, and immunostained with a anti-p24 (capsid) polyclonal antibody (anti-rabbit) and then a second dairy antibody, biotinylated anti-rabbit IgG. As a result, it was found that that Gag protein was expressed in the transfected BHK-21 cells (refer to FIG. 7, A: negative control, BHK-21 cells not transfected; B: BHK-21 cells transfected with pSFV/gag; C: BHK-21 cells transfected with pSFV/gagpro). Gag proteins were detected in the cytoplasm, and VLPs were isolated form supernatant from the cultivated medium by using the method from Example 2, and observed under an electron microscope (FIG. 8, A: VLPs from pSFV/gag; B: VLPs from pSFV/gagpro). It was found that VLP (HIVLPgag) composed of only Gag proteins was produced even when pSFV/gag or pSFV/gagpro RNA transcripts were expressed without pSFV-helper RNA transcripts.

EXAMPLE 4

Construction of pSFV/env Expression Vector

To amplify a gp160 gene of HIV, PCR was performed with a primer set consisting of primers 4 and 5, below, using HIV clade E genome (Genbank accession No. U51188, Journal of Virologly, 1996), containing a gp 160 gene between 6264 to 8879 bp, as a template.

```
Primer 4: sense (SEQ ID NO.: 4)
5'-CGCGCCTCGAGCGGGATCCCATGAGAGTGAAGGGGACACGGA-3'

Primer 5: antisense (SEQ ID NO.: 5)
5'-AATGGATCCTATAGCAAAGCCCTTTCCAAGCCC-3'
```

Figure 9:
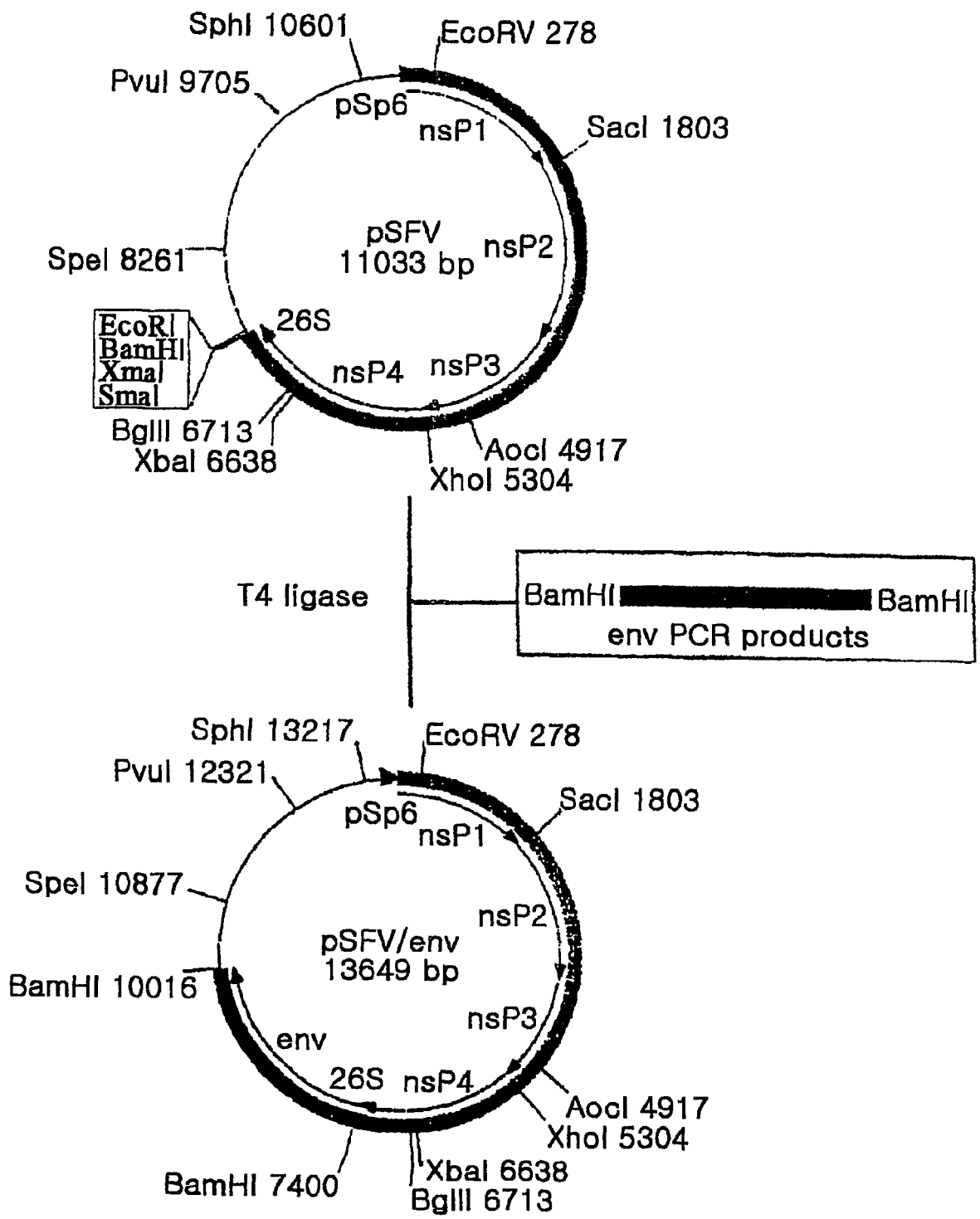

A PCR mixture was prepared as follows: plasmid pUHD (100 ng/μl) carrying full-length HIV-1 clade E genome, used as the template, was mixed with 4 μl of 2.5 mM dNTP (BM, Germany), 1 μl of sense primer (100 pmol/μl), 1 μl of antisense primer (100 pmol/μl), 5 μl of Taq polymerase 10× buffer, and 37 μl distilled water. The PCR mixture was pre-incubated at 98° C. for 5 min, and then supplemented with 1 μl of Taq polymerase, followed by a PCR reaction of 30 cycles in which each cycle was composed of 1 min at 94° C., 2 min at 55° C., and 3 min at 72° C. The amplified product for gp160 gene was cloned into BamH I site of pSFV vector, giving a recombination vector, pSFV/env (refer to FIG. 9).

EXAMPLE 5

Production of VLP using pSFV/helper and pSFV/env Expression Vectors

Figure 10:
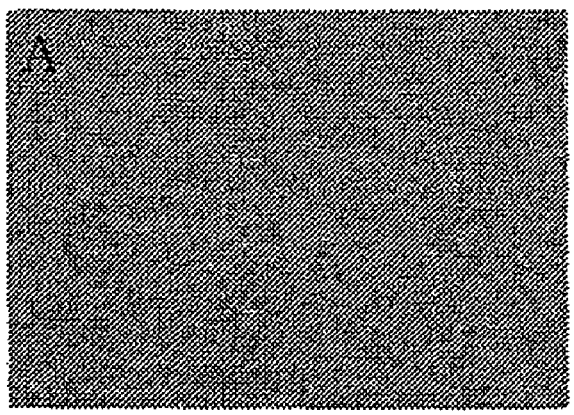
Figure 10:
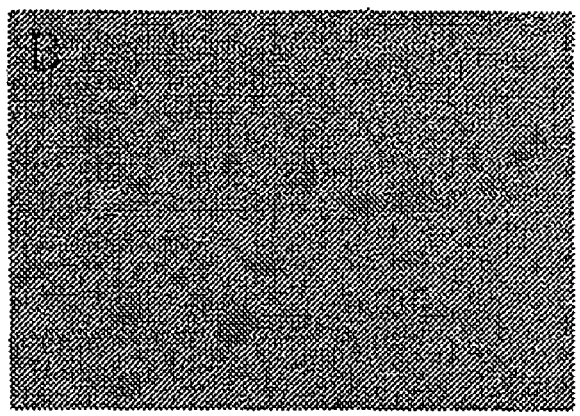

Because only Env of HIV-1 cannot produce VLP, VLP was prepared from pSFV-helper and pSFV/env. The vector of pSFV/env prepared in Example 4 was completely linearized with SpH I and purified by phenol/chloroform extraction. To obtain RNA transcripts of an env gene, a reaction mixture was prepared from 10 µl of the linearized plasmid DNA, 5 µl of 10×SP6 buffer (TaKaRa), 5 µl of 10 mM m7G(5')ppp(5')G (BM), 2.5 µl of 100 mM DTT, 5 µl of rNTP mix (10 mM ATP, 10 mM CTP, 10 mM UTP, 5 mM GTP, BM), 2 µl of Rnasin (BM), 1.5 µl of SP6 RNA polymerase (TaKaRa), and 19 µl distilled water, and incubated at 37° C. for 1 hour 30 min. Transfection was then performed according to the same electroporation as Example 2, with the exception of the use of 50 µl of pSFV/env RNA transcripts and 25 µl of pSFV/helper RNA transcripts as RNA transcripts. 48 hours after transfection, the cultivated medium was centrifuged at 3500 rpm for 15 min and the supernatant was then ultra-centrifuged (2 hr, 30,000 rpm, 4° C.) using a Beckman SW41 rotor, giving a pellet containing viral particles. The pellet was resuspended in TNE buffer (50 mM Tris-HCl, pH 7.4, 100 mM NaCl, 0.5 mM EDTA) and stored at −70° C. Also, the transfected cells were fixed with cold absolute methanol, cooled at −20° C., for 4 to 6 min, blocked with 1% gelatine, and immunostained with an anti-gp160 monoclonal antibody (1 mg/ml) and secondarily with biotinylated anti-mouse IgG (5 µl/ml). The infected cells were then incubated with an AB solution (5 µl avidin, 5 µl biotin/1 ml PBS, VECTOR) for 30 min and color was developed with a DAB (3,3'-diaminobenzidine) solution (VECTOR) (refer to FIG. 10, A: a negative control, non-transfected BHK cells; B: BHK cells transfected with pSFV/env vector). As a result, ti was found that Env protein was expressed in the transfected BHK-21 cells with pSFV/env vector.

Figure 11:
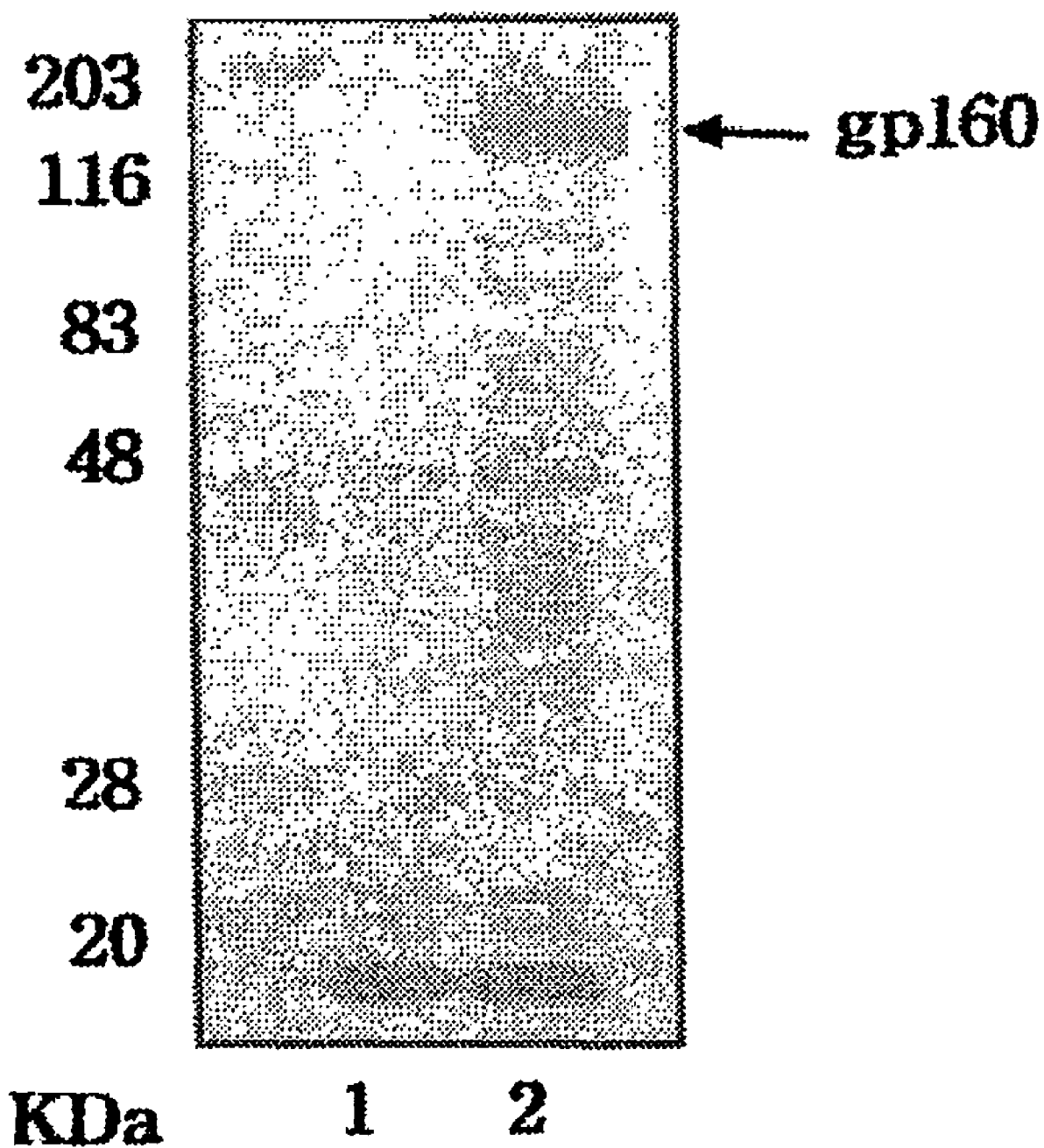

To activate VLPs, 100 µl of suspension of viral particles in TNE buffer was incubated with 5 µl of chymotrypsin (10 mg/ml), 5 µl of 50 mM CaCl$_2$ for 30 min on ice, and 45 µl of Aprotinin (2 mg/ml, Sigma, USA) was then added to terminate the protease activity. The activated VLPs were added to monolayered BHK-21 cells with 70% confluency and then incubated for 90 min at 37° C. under 5% CO$_2$, allowing for infection of BHK-21 with the VLPs. Culture medium was then aspirated, and a new medium was refed and incubation was preceded for 48 hours. After incubation, BHK-21 cells were lysed with 200 µl of a lysis buffer (1% NL40, 50 mM Tris-HCl, pH 7.6, 150 mM NaCl, 2 mM EDTA, 1 µg/ml PMSF), and centrifuged (12000 rpm, 5 min, 4° C.). the Supernatant was mixed with a sample buffer and the boiled for 5 min. The denatured samples were separated by SDS-PAGE (12%). The separated proteins were transferred onto a PVDF membrane (BM) for 2 hrs under a condition of 15 V and 7 mA, and Western blotting was performed using specific antibodies, where serum for AIDS patients was used as a first antibody and biotinylated anti-human IgG as a second antibody. The membrane was then reacted with an avidin-biotin solution and the color was developed with DAB solution (refer to FIG. 11, lane 1: a negative control, BHK-21 cells; lane 2: BHK-21 cells transfected with VLP). As a result that BHK-21 cells were infected with in vitro activated VLPs, it was found that Env proteins were produced in cytoplasm of BHK-21 cells, demonstrating production of infectious SFVLPenv.

EXAMPLE 6

Production of VLP Using pSFV/gag and pSFV/env Expression Vectors

Figure 12:
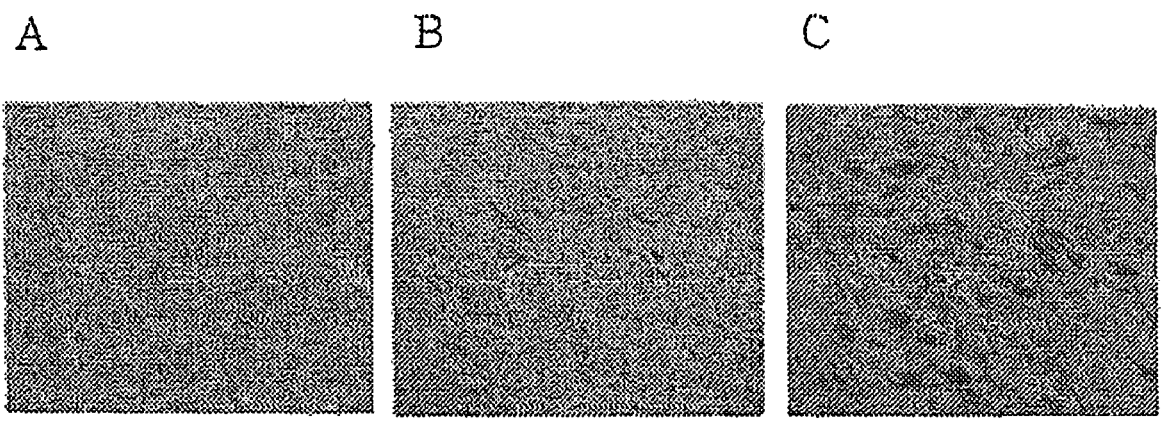

It is well known that Gag protein of HIV directs assembly of immature VLP and Env protein of HIV is a major target for development of neutralizing antibodies (Gheysen D. et al., Cell, 59, 103-112 (1989); Lasky, L. A. et al., Science, 249, 932-935 (1986); Lasky, L. A. et al., Cell, 50, 975-985 (1987)). Therefore, in order to incorporate Env protein into viral particles composed of Gag protein, RNA transcripts of pSFV/gag prepared in Example 1 and pSFV/env prepared in Example 4 were co-transfected into susceptible host cells. The expression vectors, pSFV/gag and pSFV/env, were transcribed in vitro according to the same method as Example 2 (without pSFV-helper), and co-transfected into BHK-21 cells. At 48 hr after transfection, the transfected cells were immunostained with AIDS patient serum and an anti-gp160 monoclonal antibody capable of recognizing Env protein. The sample immunostained with the AIDS patient serum (refer to C of FIG. 12) showed much more staining than that with the anti-gp160 antibody (refer to B of FIG. 12). This result indicates that there was produced HIVLP composed of Gag and Env proteins of HIV-1 (FIG. 12 A: negative control; B: anti-gp160 monoclonal antibody; C: AIDS patient serum).

EXAMPLE 7

Analysis of HIV-Like Particle-Associated Nucleic Acids

We investigated whether VLPs prepared in Examples 3 and 6, through transfection with only pSFV/gag RNA transcripts, or co-transfection with both pSFV/gag and pSFV/env RNA transcripts, repetitively, carry nucleic acid or not. The VLPs were passed through a 10% sucrose cushion. Other RNA and DNA contamination was eliminated by a digestion with 1 mg RNase A and 70 Unit of RNase-free DNase I at room temperature for 1 hr in a Mg2SO4-acetate buffer. RNA was purified with a viral RNA purification kit (Viogene), and PCR was then carried out using the purified RNA, where there was amplified a mRNA fragment of 650 bp in size as a product for gag, especially p24, and a mRNA fragment of 350 bp as a product for env. For RT-PCR of the purified RNA, the RNA was mixed with 4 µl of 5 Superscript II reverse transcriptase buffer (250 mM Tris-HCl, pH 8.5, 375 mM KCl, 15 mM MgCl$_2$), 2 µl of 0.1 M DTT and 4 µl of deoxynucleoside triphosphates (dNTP, 25 mM each; TaKaRa) and a primer, and distilled water up to 20 µl. The mixture was incubated for 2 min at 42° C., and supplemented with 1 µl of superscript II reverse transtriptase (from pol gene of Molony Murine Leukemia virus (Gibco BRL), followed by incubation for 50 min at 42° C. to give first DNA strands in the form of a RNA/DNA hybrid. Herein, there were used 1 µl of Primer 6 of 100 pmol for gag RNA, 1 µl of Primer 7 of 100 pmol for env RNA.

```
Primer 6: antisense (SEQ ID NO.: 6)
5'-CCCAAGCTTTTAGCATGCTGTCATCATTTC-3

Primer 7: antisense (SEQ ID NO.: 7)
5'-GGTTCTGCAGAAGCTTCCTTGTTATTTCAAACCA-3
```

The RNA/DNA hybrids were denatured and the reverse transtriptase was inactivated by incubation for 15 min at 70°

C. DNA amplification was done with Z tag DNA polymerase (TaKaRa) and a primer set (Primer 8 and Primer 6 for gag RNA detection; Primer 9 and Primer 7 for env RNA detection) using cDNA made from the above RT-PCR as a template. Herein, 10 μl of the template cDNA was mixed with 4 μl of 2.5 mM dNTP (BM, Germany), 1 μl of sense primer (100 pmol/μl), 1 μl of antisense primer (100 pmol/μl), 5 μl of 10×Z Taq polymerase buffer, 28 μl of distilled water and 1 μl of Z Taq polymerase (TaKaRa). The PCR mixture was pre-incubated for 5 min at 94° C. for denaturation, and then PCR was performed with 35 cycles where each cycle consisted of 1 min at 94° C., 1 min at 55° C., and 1 min 72° C., followed by incubation of 7 min at 72° C.

```
Primer 8: sense (SEQ ID NO.: 8)
5'-CCCAAGCTTCATCAGGCCTTATCACCT-3

Primer 9: sense (SEQ ID NO.: 9)
5'-TCCCCCGGGAAGCTTGCGCAGCAGCATCTGTTG-3
```

Figure 13:
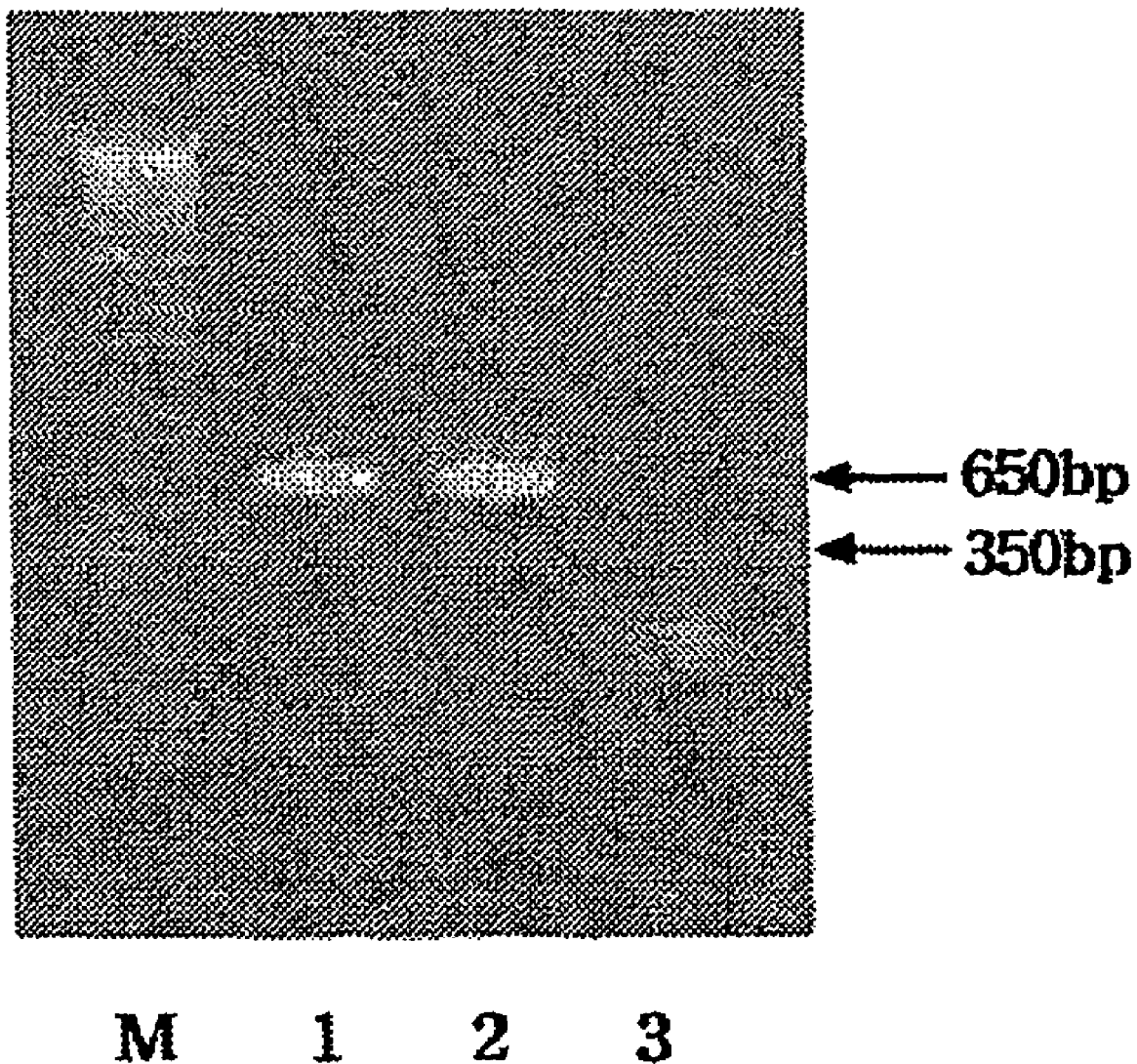

The amplified products were applied to an agarose gel and visualized under UV illumination after ethidium bromide staining. It was found that a p24 gene was amplified at HIVLP gained after transfection of only pSFV/gag RNA transcripts as well as HIVLP gained after co-transfection of both pSFV/gag and pSFV/env RNA transcripts (refer to lanes 1 and 2 in FIG. 13). In contrast, amplification of the gp41 gene was not detected at all in the two VLPs (refer to lanes 1 and 3 in FIG. 13). This result suggests that only RNA corresponding to the gag gene was packaged into VLPs (refer to FIG. 13, lane 1: VLP from pSFV/gag; lanes 2 and 3: VLP from co-transfection of pSFV/gag and pSFV/env; lanes 1 and 2 were amplified with the use of primers for p24, lane 3 was amplified by the use of primers for gp41; a 650 bp fragment is a PCR product for gag gene and a 350 bp fragment for the env gene).

EXAMPLE 8

Production of VLP By Infection of Defective SFVLP

We investigated whether or not VLPs were produced when VLPs obtained from Examples 2 and 5 were in vitro activated and infected COS-1 cells. After cell lysate and VLPs were obtained from the supernatant of a cultivated medium, prepared from the infected COS-1 cell with VLP from Example 2 or 5, they were analysed by western-blot with AIDS patient serum, anti-p24 polyclonal antibody (anti-rabbit) and anti-p24 monoclonal antibody (refer to FIG. 14, A: AIDS patient serum; B: anti-p24 polyclonal antibody; C: anti-p24 monoclonal antibody; a negative control (lanes 1, 4, 7, 10 and 13); infection with SFVLPgag (lanes 2, 5, 8, 11, and 14); co-infection with SFVLPgag and SFVLPenv (lanes 3, 6, 9, 12, and 15); cell lysate (lanes 1, 2, 3, 7, 8, 9, 10, 11, and 12); VLP (lanes 4, 5, 6, 13, 14, and 15)).

Figure 14:
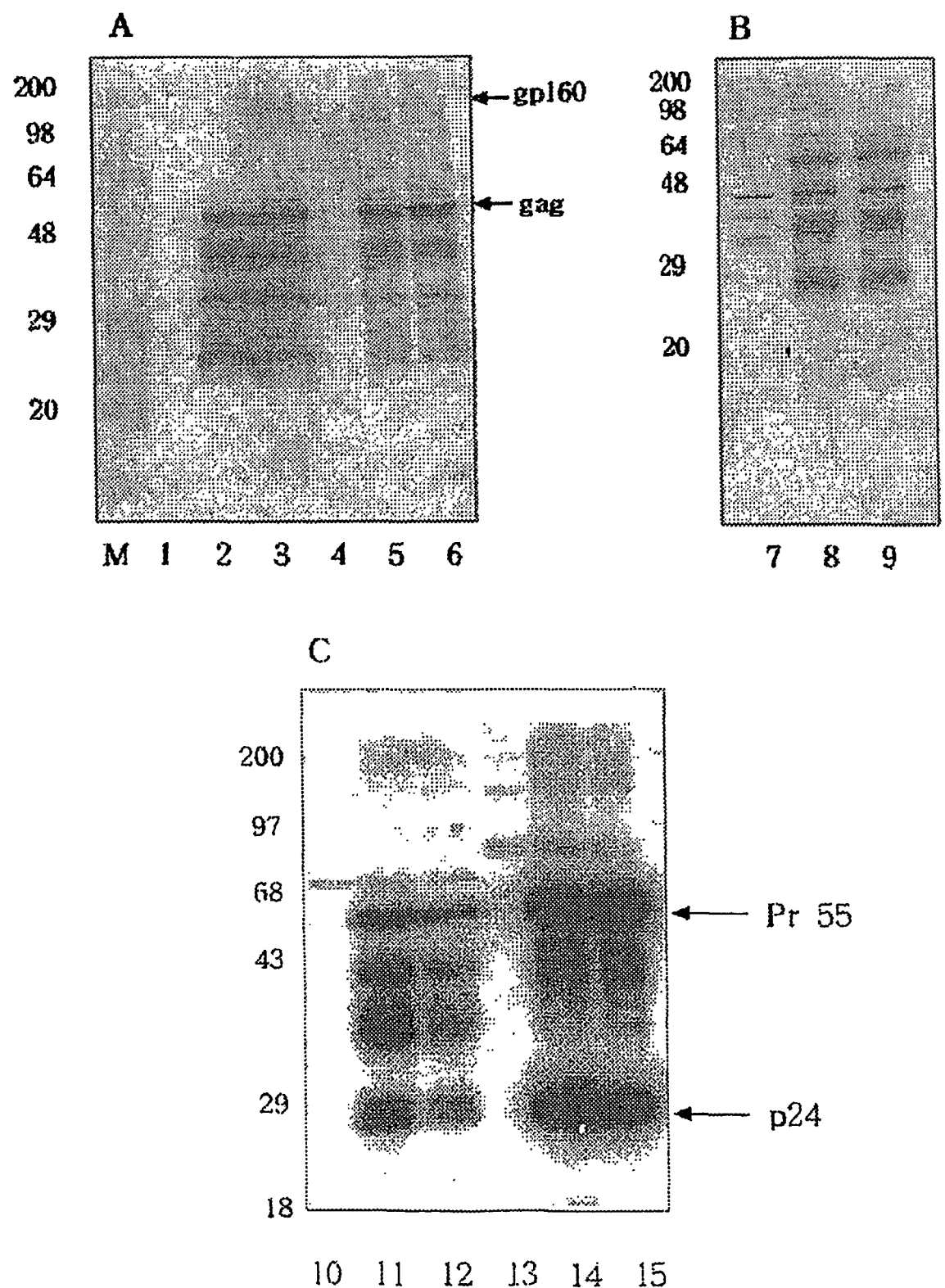

As shown in A and B in FIG. 14, when COS-1 cells infected with the defective SFVLP containing the gag gene, Gag protein was detected in the cytoplasm of COS-1 cells (lanes 2, and 8) and VLPs from supernatant. In addition, both Gag and Env proteins were detected in the cytoplasm of COS-1 cells (lanes 3, and 9) and VLPs from supernatant (lane 6) when COS-1 cells co-infected with SFV replicon containing both each gag and env genes. Accordingly, it was confirmed that, when Gag and Env proteins were simultaneously expressed in a cell, VLPs composed of the two proteins were produced. As shown in C of FIG. 14, upon Western blotting with an anti-p24 monoclonal antibody (Biogenesis, Cat. No. 4999-8607), there was detected a Gag precursor Pr55 and p24 proteins. This explains that a Gag precursor could be processed or denatured in COS-1 cells without protease of HIV-1.

EXAMPLE 9

Construction of Expression Vectors, pSFV/env-gag and pSFV/env-gag-pro

To obtain a pro gene (from 2268 to 2606 bp in HIV-1 clade E genome) containing a 26S subgenomic promoter, PCR was performed with a mixture consisting of, pUHD (100 ng/μl) containing whole HIV-1 Clade E genome, 4 μl of 2.5 mM dNTP (BM, Germany), 1 μl of sense primer (100 pmol/μl), 1 μl of antisense primer (100 pmol/μl), 5 μl of 10×Taq polymerase buffer, 37 μl distilled water, and 1 μl of Taq polymerase, and a thermal cycle of 1 min at 94° C., 1 min at 55° C., and 1 min 72° C. was repeated 40 times.

```
Primer 10: sense (SEQ ID NO.: 10)
5'-CCAAGATCTATGACAGCCTCCTCCTTTAGTTTC-3'

Primer 11: antisense (SEQ ID NO.: 11)
5'-CAACCCGGGTCGCGATTAAGTGTCAATAGGACTAAT-3'
```

Figure 15:
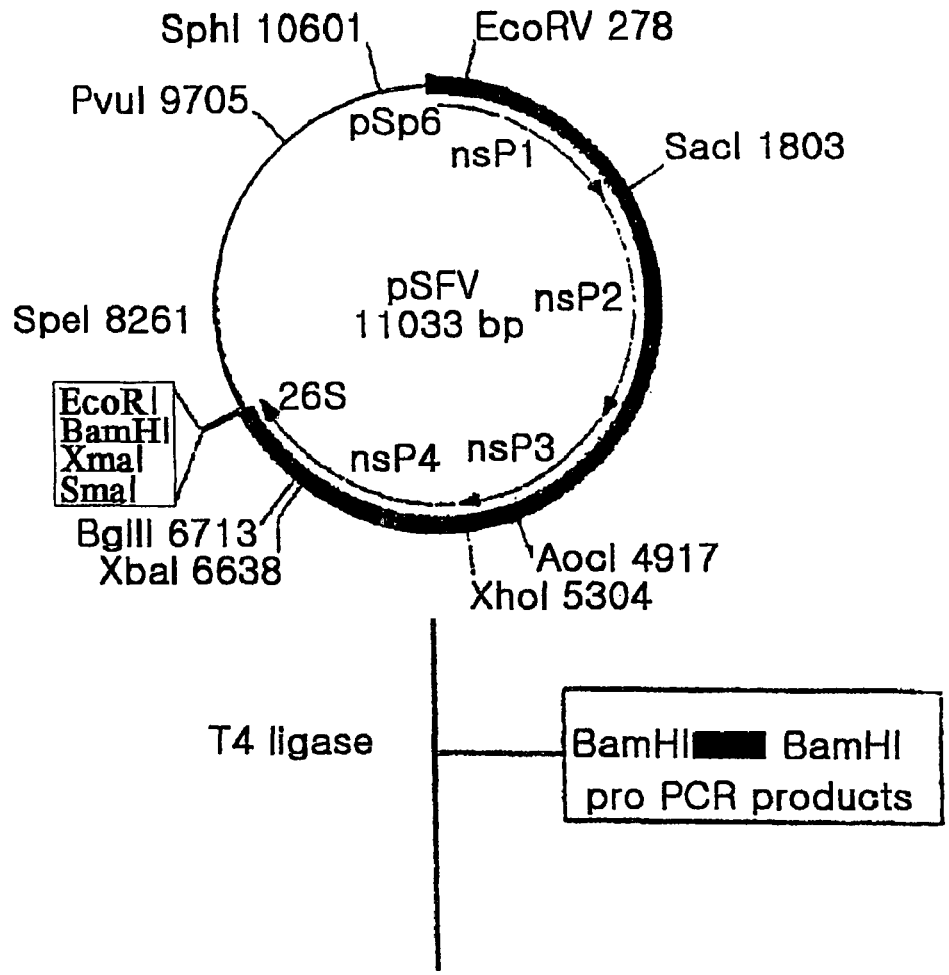
Figure 15:
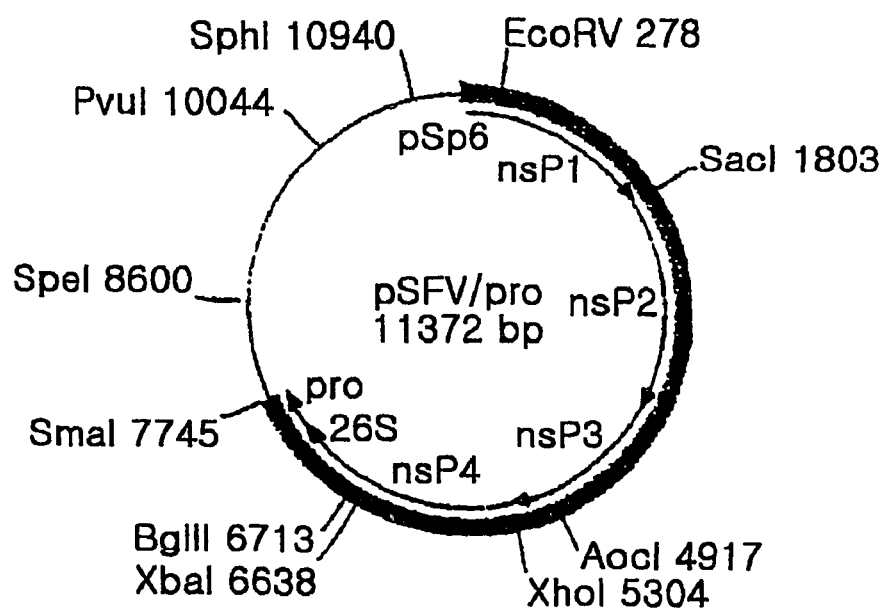
Figure 16:
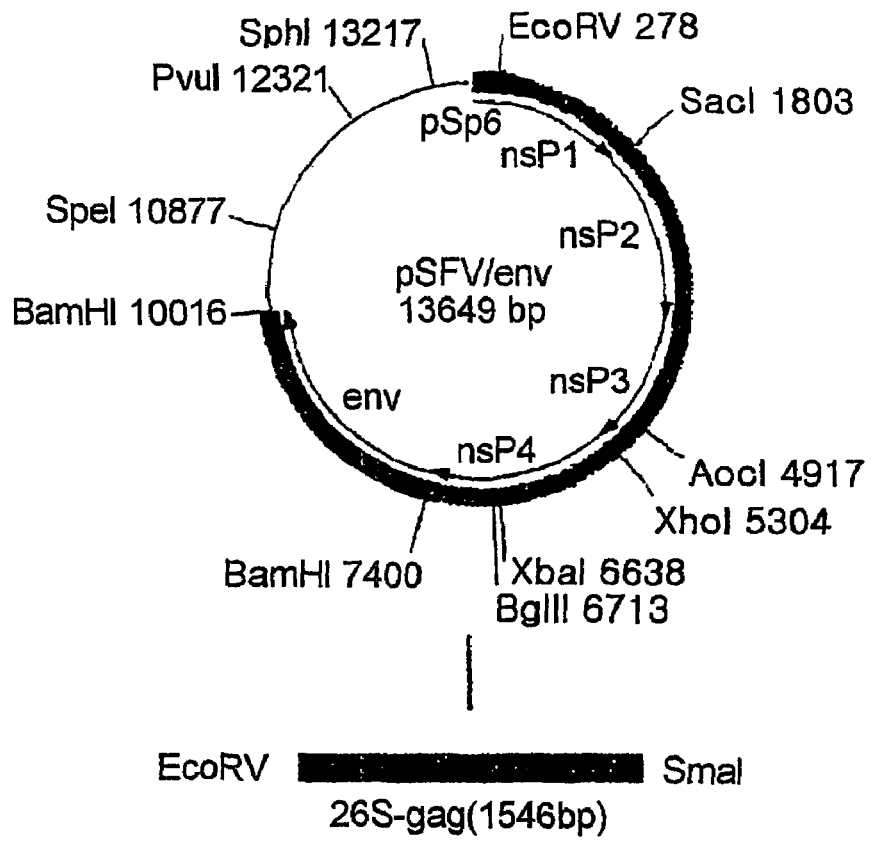
Figure 16:
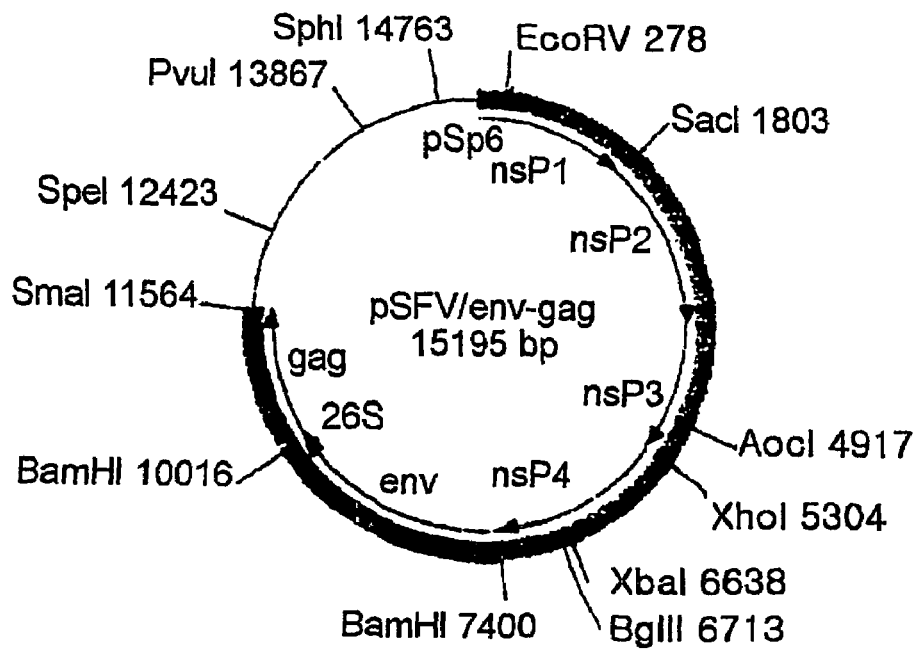

The amplified product of the pro gene was cloned into a SmaI site of a multicloning site of pSFV using EcoRV and a SmaI recognition sequence in both ends of the primers, generating pSFV/pro vector (refer to FIG. 15). To construct pSFV/env-gag vector, a 26S gag gene was primarily amplified using the vector pSFV/gag prepared in Example 1 as a template, in the presence of Primer 12 (sense) for 26S subgenomic promoter and Primer 2 (antisense) for a gag gene. The amplified 26S gag gene was then inserted into the SmaI site of the vector pSFV/env (refer to FIG. 16).

```
Primer 12: sense (SEQ ID NO.: 12)
5'-CCGGATATCACCTCTACGGCGGTCCTA-3'

Primer 13: antisense (SEQ ID NO.: 13)
5'-CGCCCGGGTTACTGTGACAAGGGGTCGTTGCCAAA-3'
```

Figure 17:
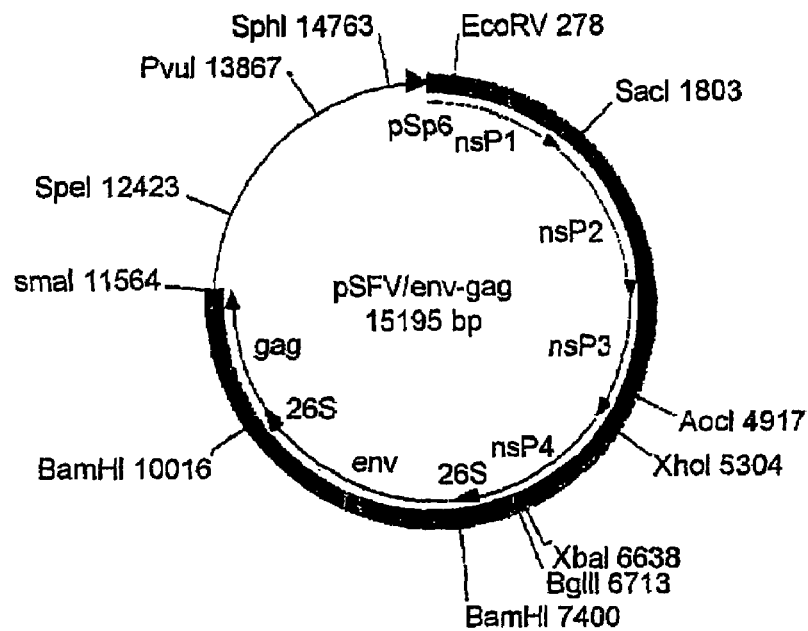
Figure 17:
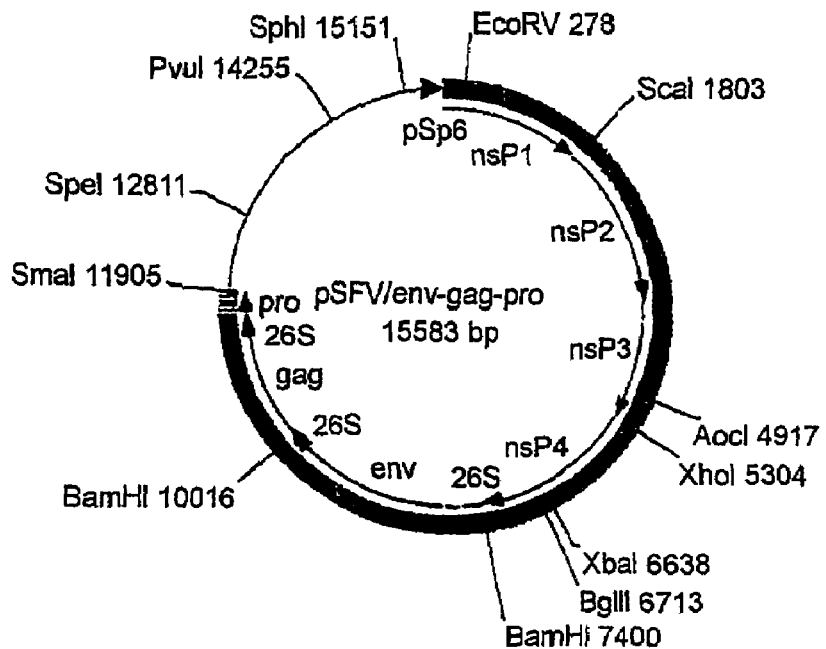

Using the pSFV/pro vector as a template, a 26S pro gene was amplified with a primer set of Primer 12 (sense) for a 26S subgenomic promoter and Primer 11 (antisense) for pro gene, and the amplified product was then inserted into the SmaI site of a pSFV/env-gag vector, giving a pSFV/eng-gag-pro vector (refer to FIG. 17). Herein, the nucleotide sequence of the amplified pro gene is in part deleted at N-terminus an gained at C-terminus, in comparison with a pro gene of gagpro in Example 1. Thus obtained sequence for a pro gene contains a nucleotide sequence necessary for self-processing (Viviane V. et al., J. Gen. Virol. 73, 639-651 (1992)). The vector pSFV/env-gag-pro was deposited with Korean Culture Center of Microorganisms (KCCM), 361-221, Yurim B/D, Hongie-1-dong, Seodaemun-gu, Seoul 120-091, Republic of Korea, one of international depository authorities, on Dec. 11, 2000, as Accession NO. KCCM-10233, under the Budapest Treaty on the International Recognition of the Deposit of Microorganisms for the purpose of Patent Procedure.

EXAMPLE 10

Production of VLP Through Expression of pSFV/env-gag Vector

Figure 18:
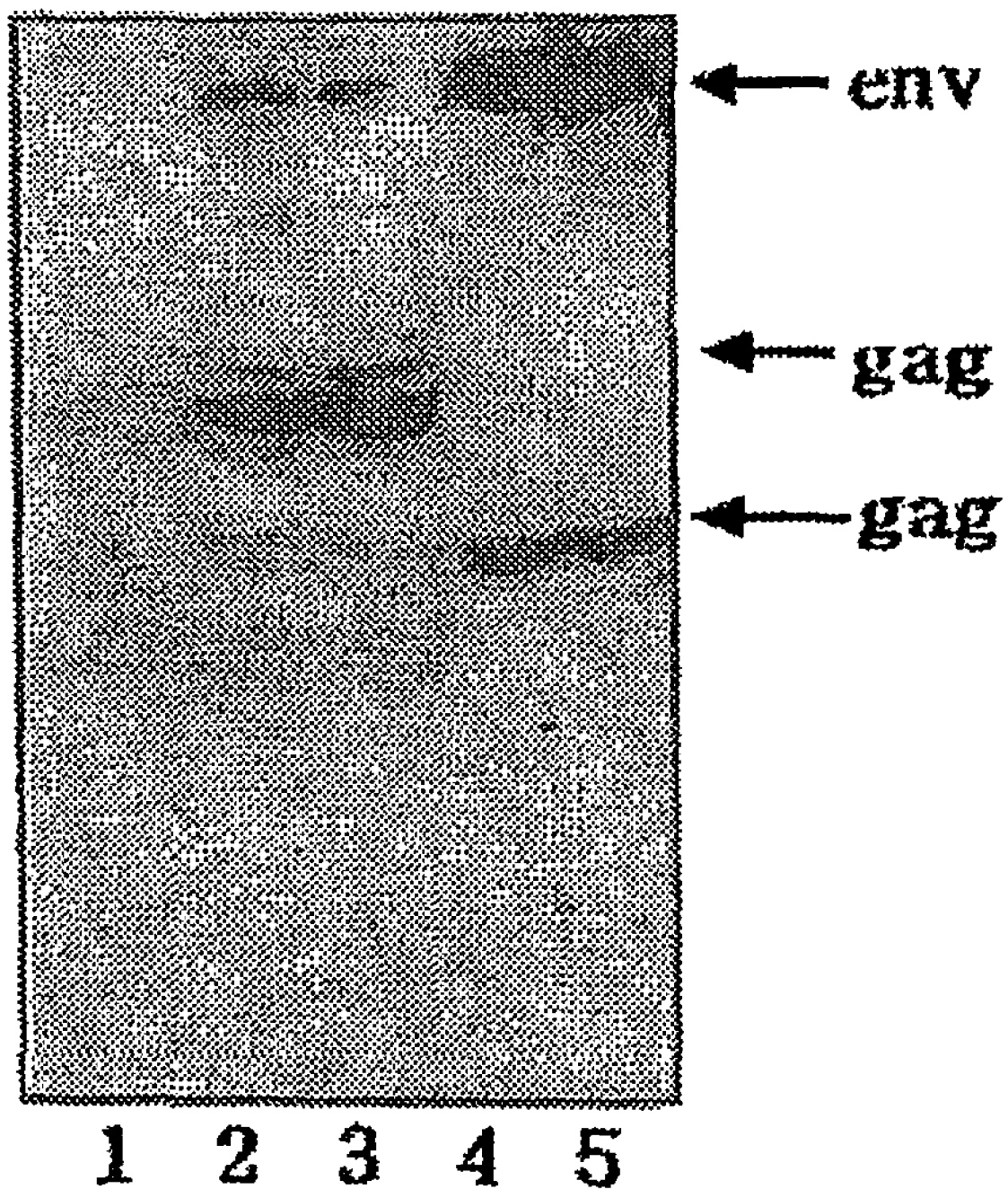
FIG. 18 is a photograph showing western blotting of cell lysates or VLPs from BKK-21, transfected with pSFV/env-gag RNA transcript, with AIDS patient serum.

To produce gag-containing VLPs into which Env protein is incorporated, the Gag and Env protein genes were cloned into a Semliki Forest Virus (SFV) replicon in the same plasmid with separate subgenomic promoters, as described in Example 9. RNA transcripts of the resulting pSFV/env-gag vector of Example 9 were transfected into BHK-21 cells. At 48 hr after transfection, the transfected cell lysates and VLPs obtained from the supernatant were analyzed by Western blot with AIDS patient serum, followed by ECL (enhanced chemiluminescence) assay (refer to FIG. 18, lane 1: negative control; lanes 2, and 3: cell lysate; lanes 4, and 5: cell supernatant). As a result, both Gag and Env proteins were detected in VLPs, demonstrating env and gag genes cloned on the sample plasmid, in which the expression of the two genes were separately controlled under different subgenomic promoters, were simultaneously expressed in the same cell, allowing production of VLP by the interaction of the two proteins. In FIG. 18, in the supernatant of a cultivated medium, band for Gag protein was shown in a slightly smaller size than in cell lysate because of being pushed by a high content of albumin of 65 kDa.

EXAMPLE 11

Production of VLP through Expression of pSFV/env-gag-pro Vector

Figure 19:
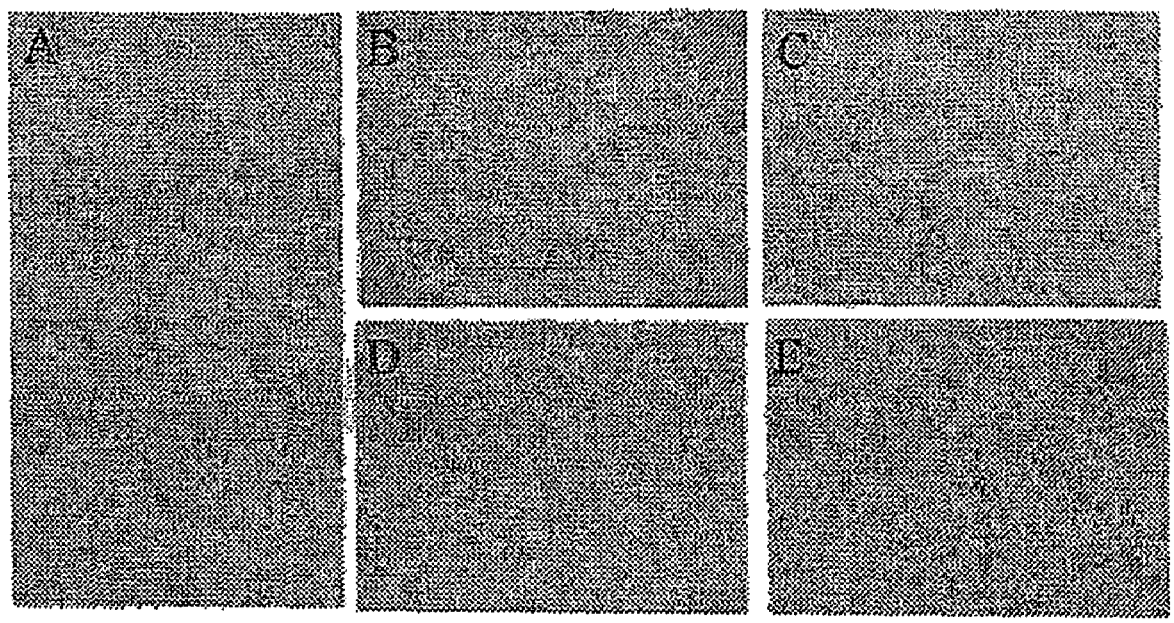
FIG. 19 is a photograph for immunocytochemistry of BHK-21 cells transfected with RNA transcript of pSFV/env-gag-pro, showing expression of Gag, Env and Pro proteins.

The pSFV/eng-gag-pro vector prepared in Example 9 was transfected into host cells and expression levels for the three genes were examined. RNA transcripts of pSFV/env-gag-pro were transfected into BHK-21 cells. At 48 hr after transfection, the transfected cells were immunostained with AIDS patient serum, anti-gp160 monoclonal antibody, anti-p24 polyclonal antibody, and anti-protease polyclonal antibody (anti-sheep) (refer to FIG. 19, A: a negative control; B: AIDS patient serum; C: anti-gp160 monoclonal antibody; D: anti-p24 polyclonal antibody; E: anti-protease polyclonal antibody). As a result, Gag, Env, and Pro proteins were all detected. Accordingly, it indicates that Gag, Env, and Pro were separately expressed under different 26S subgenomic promoters, demonstrating that there can be expressed each of three foreign genes, separately linked to a subgenomic promoter of an alphavirus-based expression vector.

EXAMPLE 12

Construction of pSFV/env-gag-gagpro-CTE Expression Vector

Figure 20:
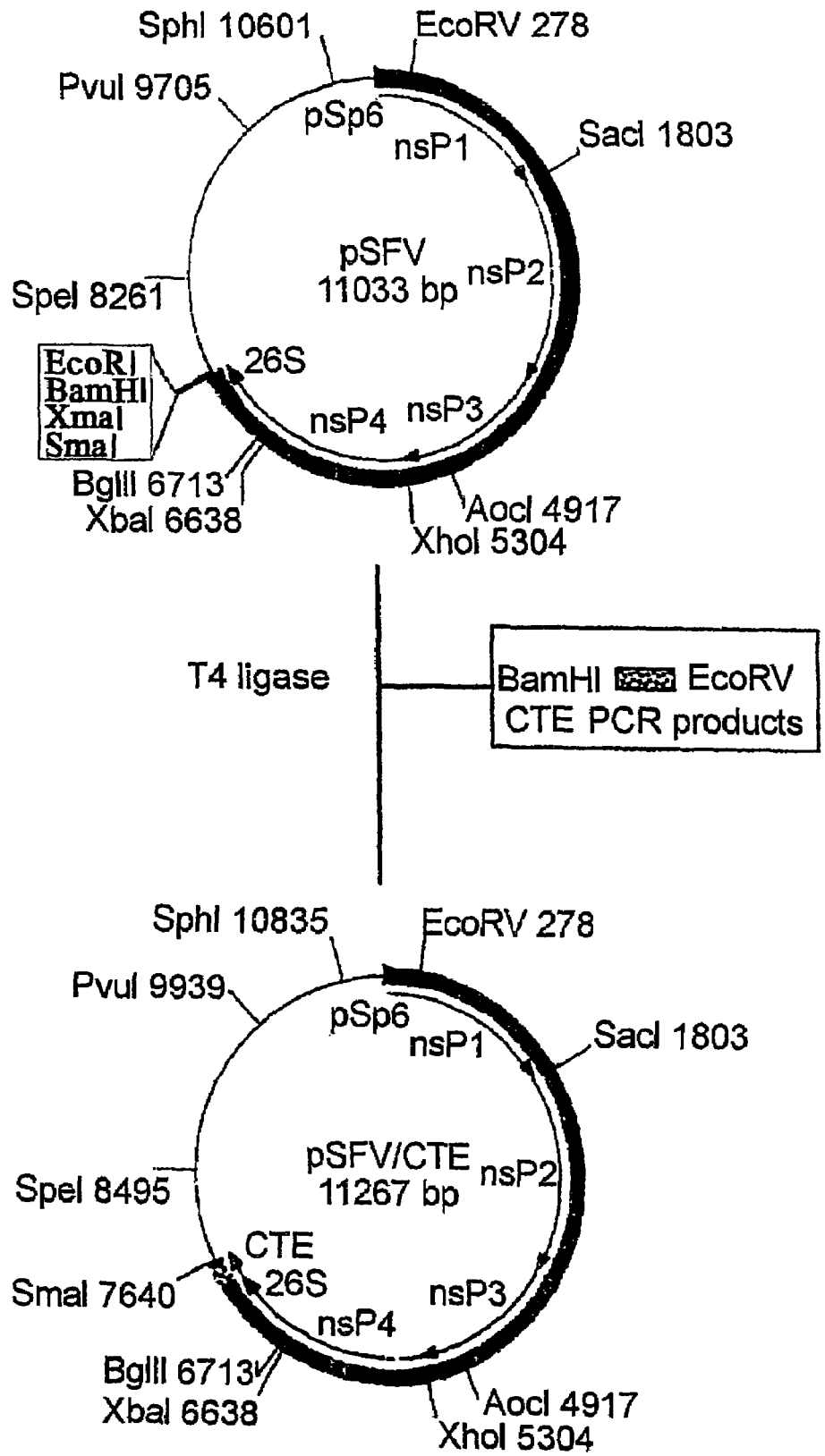
FIG. 20 is a schematic diagram showing a process for construction of an expression vector pSFV/CTE.
Figure 21:
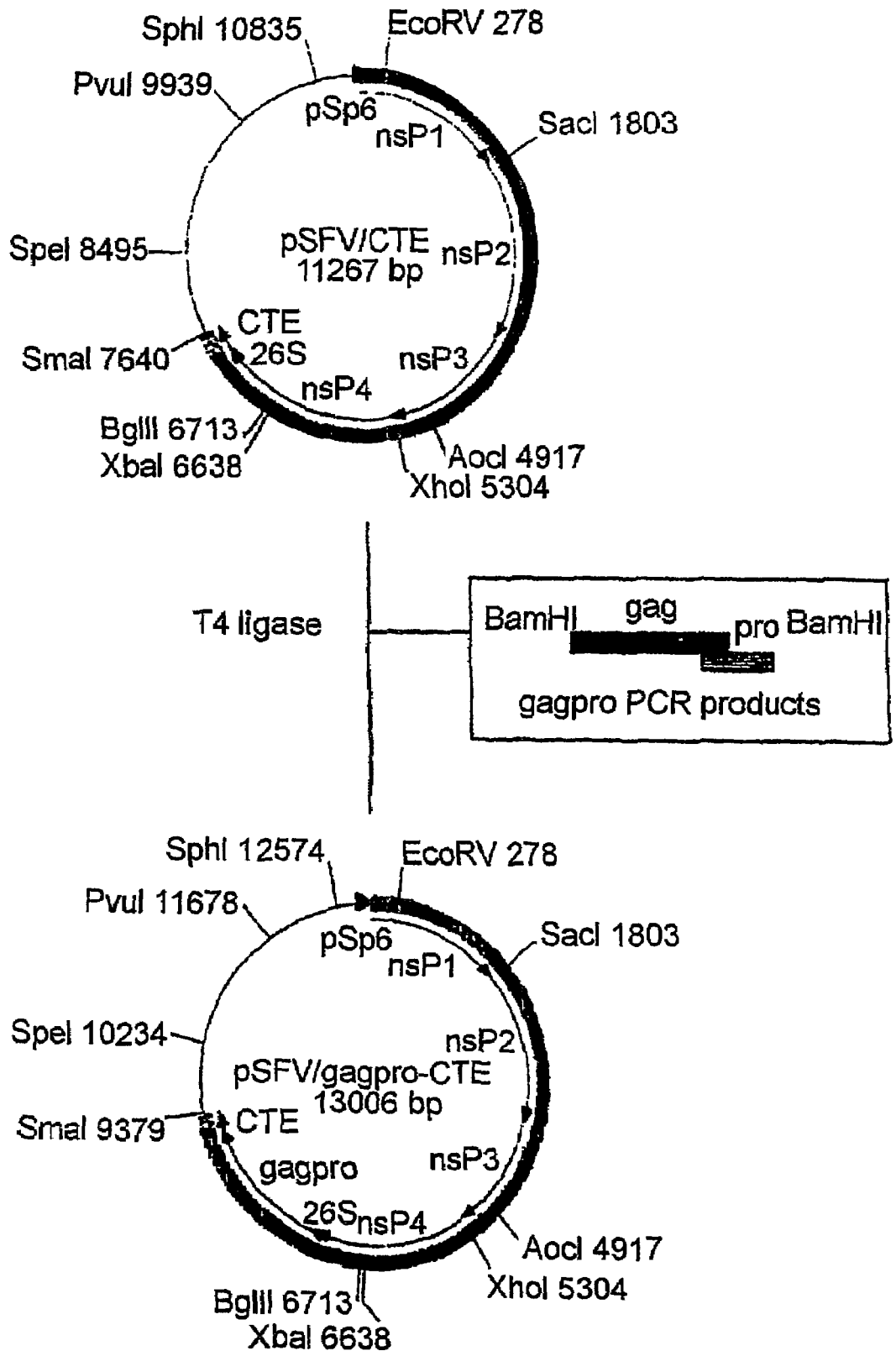
FIG. 21 is a schematic diagram showing a process for construction of an expression vector pSFV/gagpro-CTE.

To primarily make a pSFV/CTE vector, PCR was performed with Primers 14 and 15 using pGEM 7fz(−)MPMV plasmid DNA as a template. The amplified CTE gene was inserted into a region between a BamHI site and a SmaI site of pSFV (refer to FIG. 20). A Gagpro gene excised from pSFV/gagpro, prepared in Example 1 by digestion with BamHI, was cloned into a BamHI site of the vector pSFV/CTE, giving pSFV/gagpro-CTE (refer to FIG. 21). A CTE gene from Maston-Pfizer monkey virus was then inserted behind a pSFV/gagpro, generating pSFV/gagpro-CTE vector.

Figure 22:
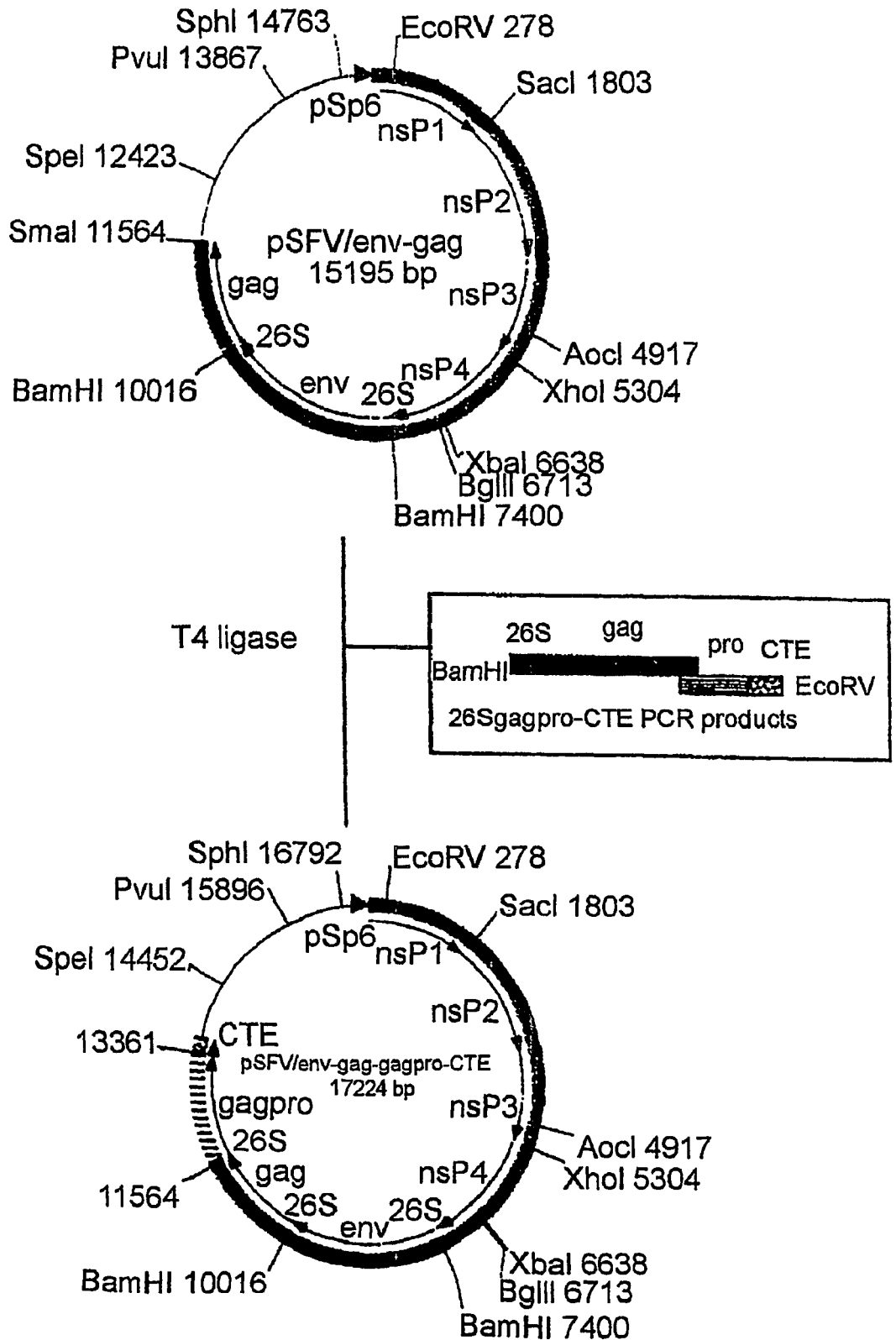
FIG. 22 is a schematic diagram showing a process for construction of an expression vector pSFV/en-gag-gagpro-CTE.

To finally construct pSFV/env-gag-gagpro-CTE, using the vector pSFV/gagpro-CTE as a template, a full-length gagpro gene containing 26S subgenomic promoter and a CTE gene were amplified by PCR with primers 12 and 15. The resulting product was inserted into a SmaI site of the vector pSFV/env-gag of Example 9 (refer to FIG. 22). A PCR mixture was prepared as follows: 1 µl of pSFV/gagpro-CTE was mixed with 4 µl of 2.5 mM dNTP (BM, Germany), 1 µl of sense primer (100 pmol/µl), 1 µl of antisense primer (100 pmol/µl), 5 µl of 10×Taq polymerase buffer and 37 µl distilled water. The PCR mixture was pre-incubated at 98° C. for 5 min, and then supplemented with 1 µl of Taq polymerase, followed by PCR reaction of 40 cycles in which each cycle consisted of 1 min at 94° C., 1 min at 55° C., and 2 min at 72° C. The vector pSFV/env-gag-gagpro-CTE was deposited with Korean Culture Center of Microorganisms (KCCM), 361-221, Yurim B/D, Hongje-1-dong, Seodaemun-gu, Seoul 120-091, Republic of Korea, one of international depository authorities, on Dec. 11, 2000, as Accession No. KCCM-10234, under the Budapest Treaty on the International Recognition of the Deposit of Microorganisms for the Purpose of Patent Procedure.

```
Primer 14 sense (SEQ ID NO.: 14)
5'-AATGGATCCCCTCCCCTGTGAGCTAGACT-3'

Primer 15 antisense (SEQ ID NO.: 15)
5'-AATGATATCAGATCTCCAAGACATCATCCGGGCAA-3'
```

EXAMPLE 13

Construction of pSFV/env-gag-gagΔpro-CTE Expression Vector gagΔpro was prepared from deletion of conserved five Ts at a signal for ribosomal frame shift from a gagpro sequence, as follows. Using the vector pSFV/gag of Example 1 as a template, amplified was a portion containing 26S subgenomic promoter and gag gene (832-2113), located upstream of site, with the use of Primer 12 and Primer 16, below. Herein, a PCR mixture was prepared as follows: 1 µl of pSFV/gag was mixed with 4 µl of 2.5 mM dNTP (BM, Germany), 1 µl of sense primer (100 pmol/µl), 1 µl of antisense primer (100 pmol/µl), 5 µl of 10×Taq polymerase buffer and 37 µl distilled water. The PCR mixture was pre-incubated at 98° C. for 5 min, and then supplemented with 1 µl of Taq polymerase, followed by a PCR reaction of 40 cycles in which each cycle consisted of 1 min at 94° C., 1 min at 55° C., and 1 min at 72° C. The amplified product was inserted into pGEMT vector (Promega). Also, a full-length pro gene, with the exception of the conserved sequence of a signal for frameshifting, was amplified using the vector pSFF/gagpro-CTE of Example 12 as a template with a primer set of Primer 15 and 17, and then inserted into pGEMT vector, according to the same procedure described above.

```
Primer 16 antisense (SEQ ID NO.: 16)
5'-AATAGGCCTGTCTTTCAGTGCAGTCTT-3'

Primer 17 sense (SEQ ID NO.: 17)
5'-CACAGGCCTATAGGGAAAATCTGGCCTTC-3'
```

Figure 23:
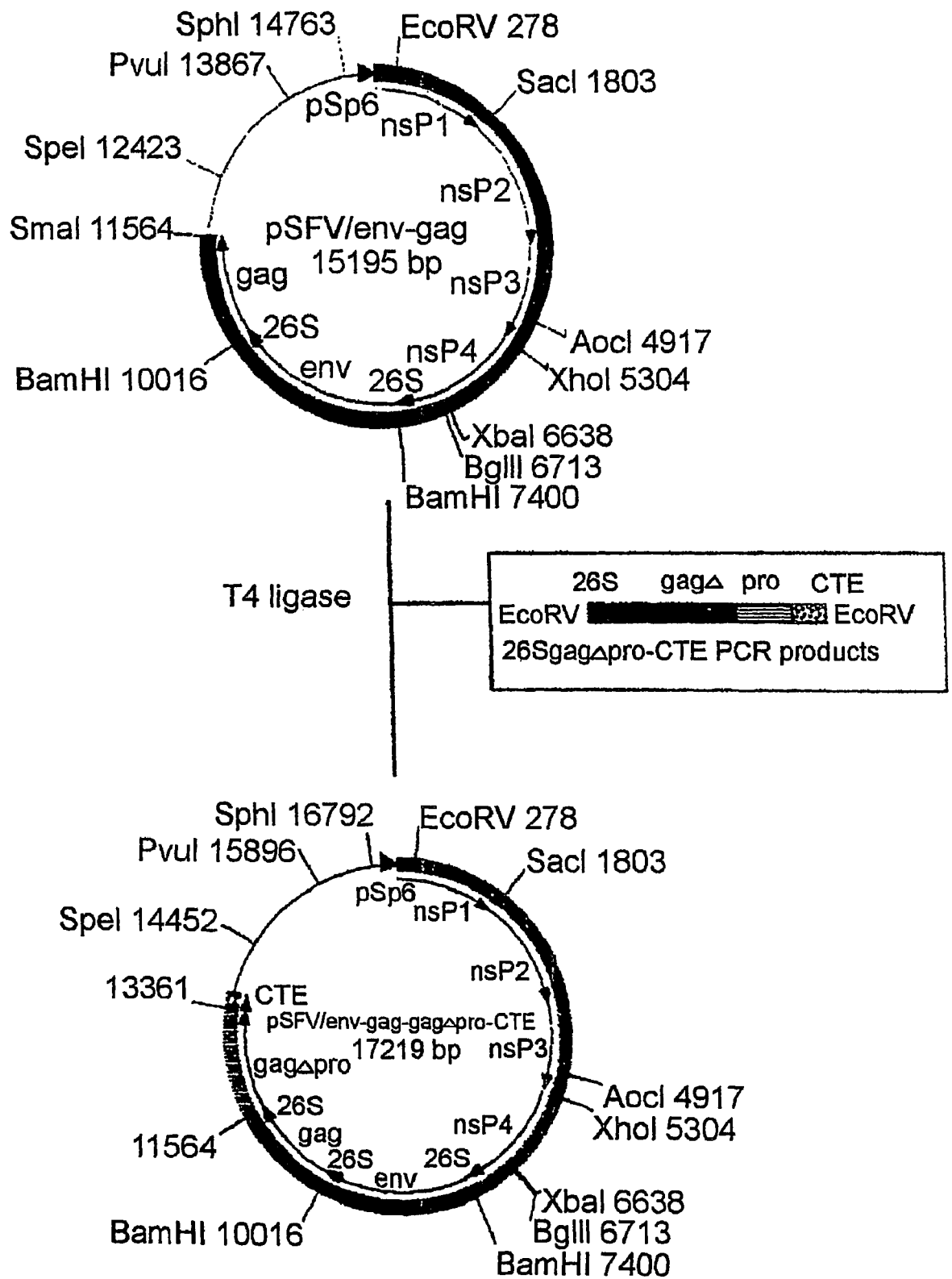
FIG. 23 is a schematic diagram showing a process for construction of an expression vector pSFV/eng-gag-gagΔ-pro-CTE, showing the insertion of gagΔpro gene, prepared from deletion of a sequence responsible for ribosomal frameshifting at 3' end of gag mRNA region into pSFV/env-gag vector.

The two obtained genes were digested with restriction enzyme StuI and ligated, generating gagΔpro. In this step, Asn (Asparagine) was substituted with Tyr (Tyrosine), and two Phe(Phenylalanine) deleted with the deletion of conserved five Ts, gagΔpro was then digested with EcoRv and inserted into a SmaI site of the vector pSFV/env-gag, giving pSFV/env-gag-gagΔpro-CTE vector (refer to FIG. 23).

```
(SEQ ID NO.: 18)    F   F   R   E
CAG GCT AATTT TTT AGG GAA    Ribosomal frame shift
                             site of gag-pol
mRNA
      Q       A    N (SEQ ID NO.: 19)
CAG GCC TAT AGG GAA          Mutation site of
                             GagΔpro

Q    A    Y   R   E
```

EXAMPLE 14

Construction of pSFV/gagpol Expression Vector

To prepare an expression vector expressing a Gagpol polyprotein, a gagpol gene of HIV-1 was inserted into an alphavirus replicon. A full-length gagpol gene (832-5132 bp) of HIV-1 was amplified by polymerase chain reaction (PCR) with Primers 18 and 19 using HIV-1 Clade E genome as a template. A PCR mixture was prepared as follows: plasmid pUHD (100 ng/μl) carrying full-length HIV-1 clade E genome, used as the template, was mixed with 4 μl of 2.5 mM dNTP (BM, Germany), 1 μl of sense primer (100 pmol/μl), 1 μl of antisense primer (100 pmol/μl), 5 μl of 10×Taq polymerase buffer and 37 μl distilled water. The PCR mixture was pre-incubated at 98° C. for 5 min, and then supplemented with 1 μl of Taq polymerase, followed by a PCR reaction of 40 cycles in which each cycle consisted of 1 min at 94° C., 1 min at 55° C., and 3 min at 72° C.

```
Primer 18: sense (SEQ ID NO.: 20)
5'-TTAGGATCCATGGGTGCGAGAGCGTCA-3'

Primer 19: antisense (SEQ ID NO.: 21)
5'-CGCGGATCCCTAATCCTCATTCTGTCTACC-3'
```

Figure 24:
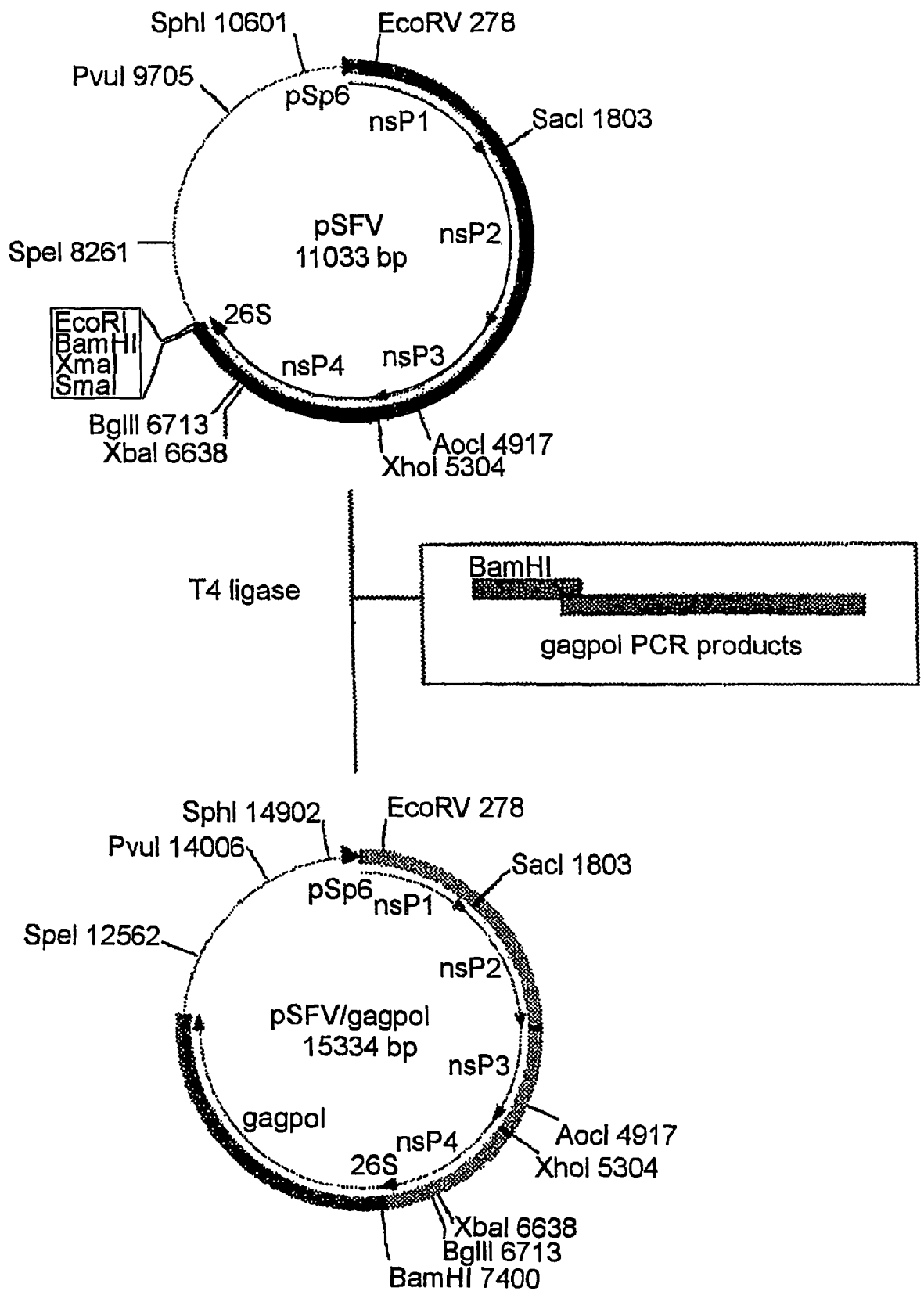
FIG. 24 is a schematic diagram showing a process for construction of an expression vector pSFV/gagpol.

The amplified product was inserted into a BamHI site of pSFV vector, giving a pSFV/gagpol vector (refer to FIG. 24).

EXAMPLE 15

Preparation of VLP using pSFV/gagpol Vector

Figure 25:
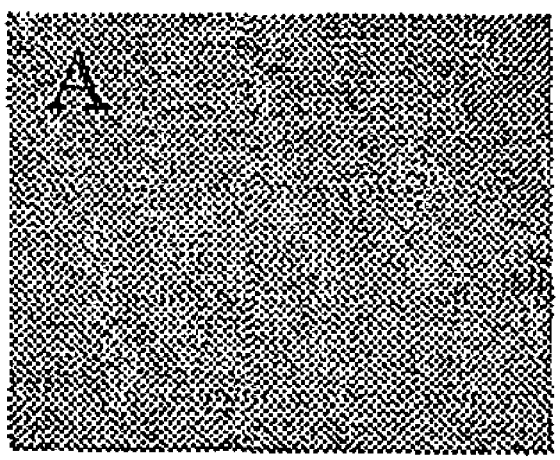
FIG. 25 is a photograph for immunocytochemistry showing expression of Gag and Gagpol polyproteins in BHK-21 cells transfected with pSFV/gagpol vector, with the use of an anti-p24 polyclonal antibody and an anti-protease polyclonal antibody.
Figure 25:
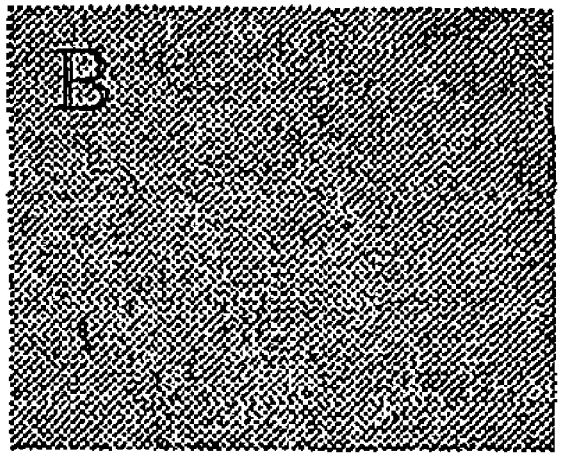
Figure 25:
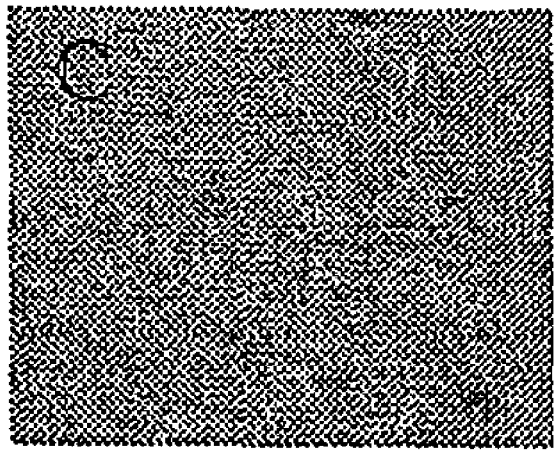
Figure 25:
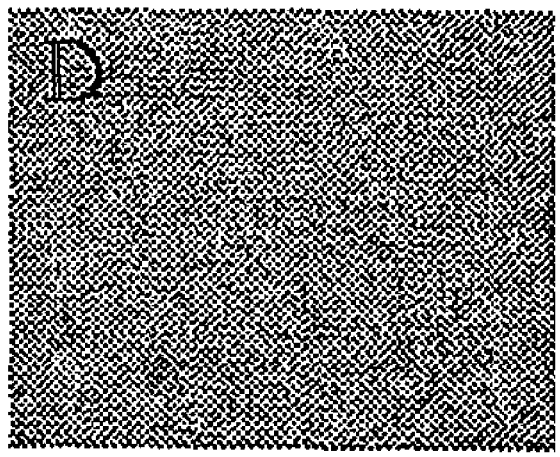

To produce VLP composed of processed HIV-1 core proteins, the vector pSFV/gagpol prepared in Example 14 was in vitro transcribed and transfected into BHK-21 cells without pSFV-helper RNA transcripts according to the same method as Example 2. The transfected cells were fixed with cold absolute methanol, cooled at −20° C., for 4 to 6 min, blocked with 1% gelatine, and immunostained with AIDS patient serum, anti-p24 polyclonal antibody and anti-pro polyclonal antibody (refer to FIG. 25, A: a negative control; B: AIDS patient serum; C: anti-p24 polyclonal antibody; D: anti-pro polyclonal antibody). It was found that Gagpol polyprotein as well as Gag protein was expressed in the transfected cells, BHK-21 cells were transfected with pSFV/gagpol RNA transcripts, after an incubation period of 48 hr, the transfected cell lysates and VLPs from the supernatant were analyzed by Western blotting with an anti-p24 polyclonal antibody, followed by ECL assay (refer to FIG. 26, lanes 1 and 4; a negative control; lanes 2 and 5: sample from pSFV/gag; lanes 3 and 6: sample from pSFV/gagpol; cell lysate (lanes 1, 2, and 3): VLP (lanes 4, 5, and 6)).

Figure 26:
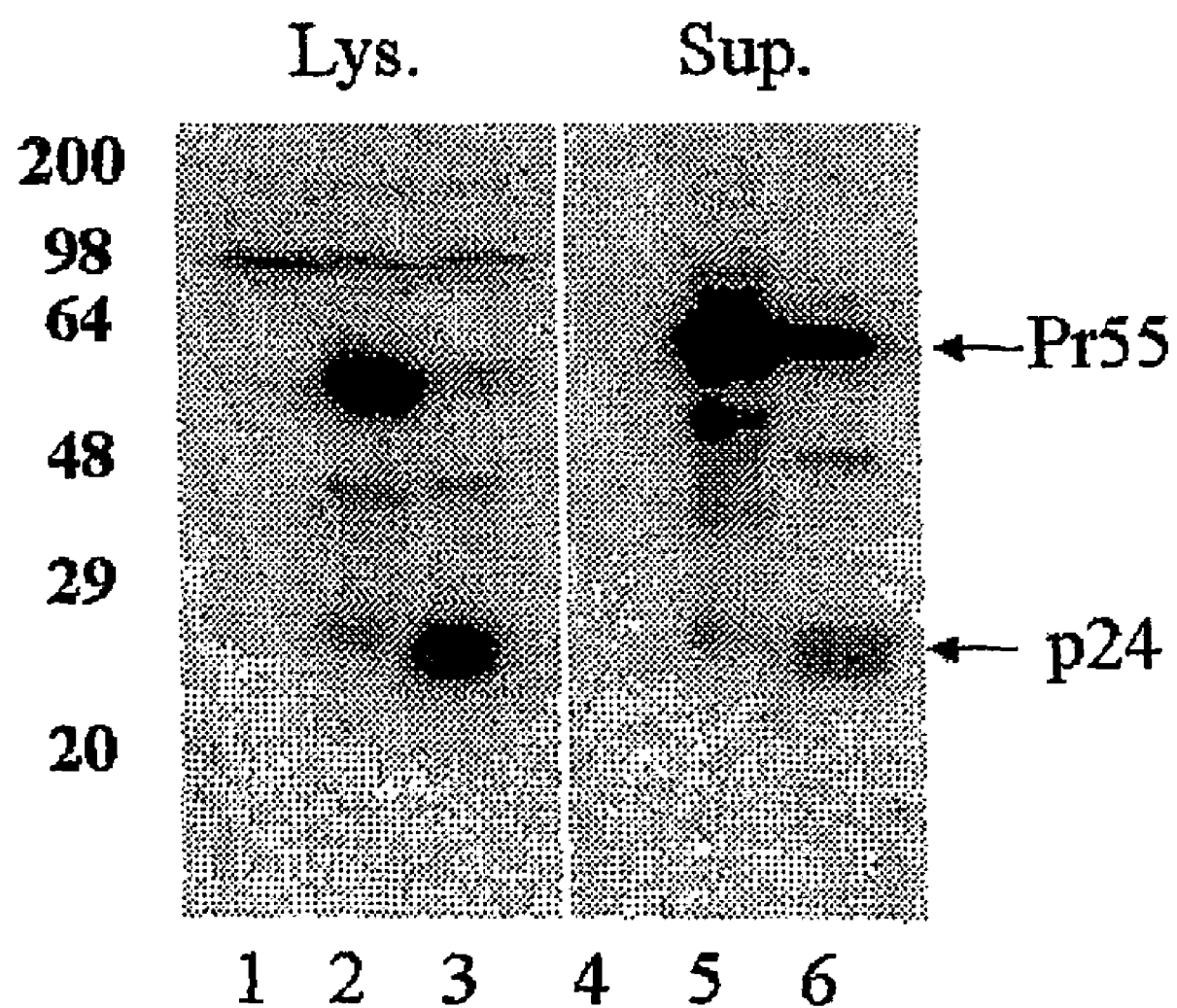
FIG. 26 is a photograph for Western blotting with anti-p24 polyclonal antibody in BHK-21 cells transfected with pSFV/gagpol RNA transcript.

As shown in FIG. 26, BHK-21 cells transfected with pSFV/gag vector expressed only Pr55 and released immature VLPs. In contrast BHK-21 cells transfected with pSFV/gagpol vector expressed p24 in addition to Pr55, and released processed mature VLPs, as a result processed Pr55 positively regulated the expression of p24.

EXAMPLE 16

Construction of pSFV/gag-envMCTE and pSFV/gagpol-envMCTE Expression Vectors

Figure 27:
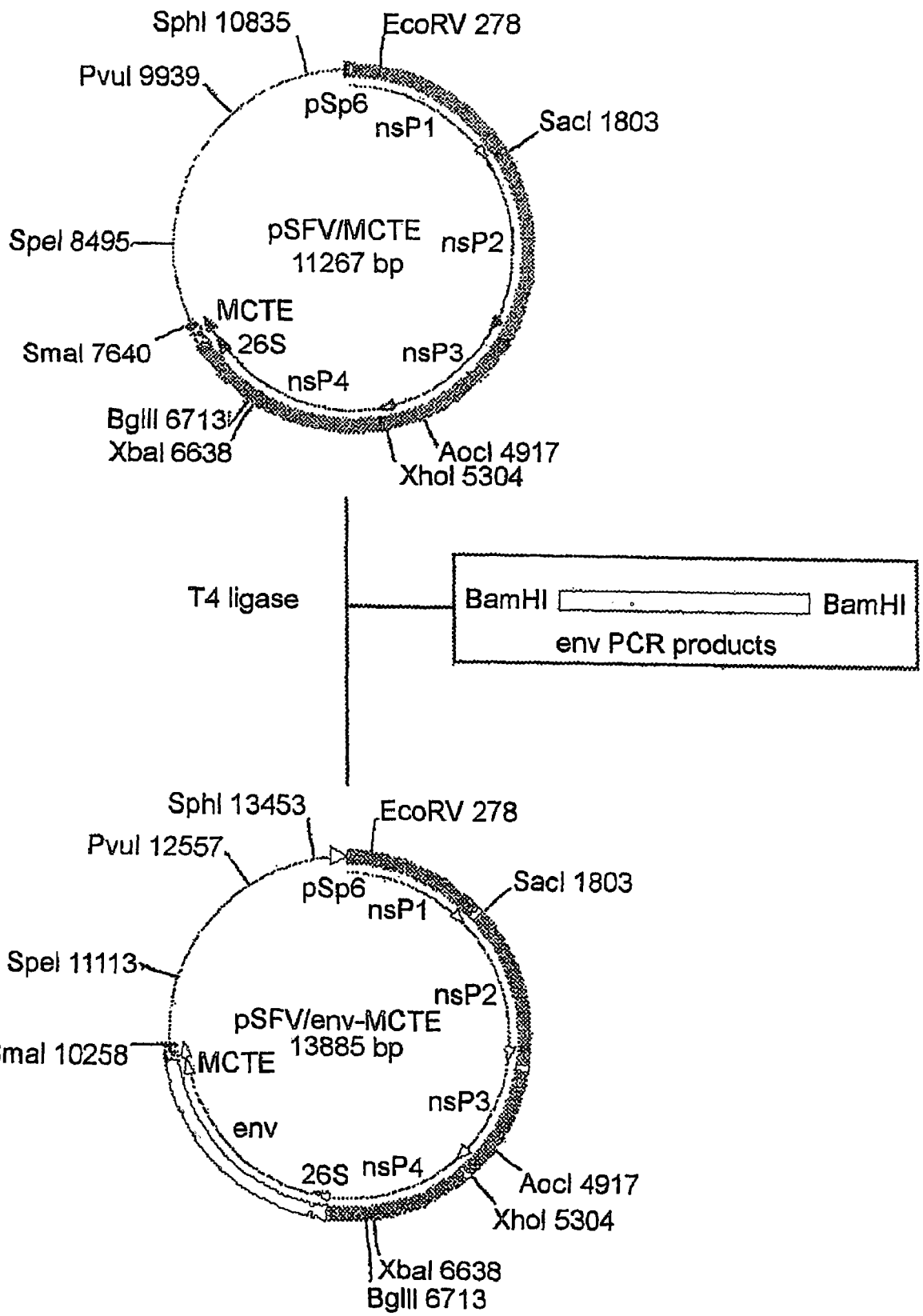
FIG. 27 is a schematic diagram showing a process for construction of an expression vector pSFV/envMCTE.
Figure 28:
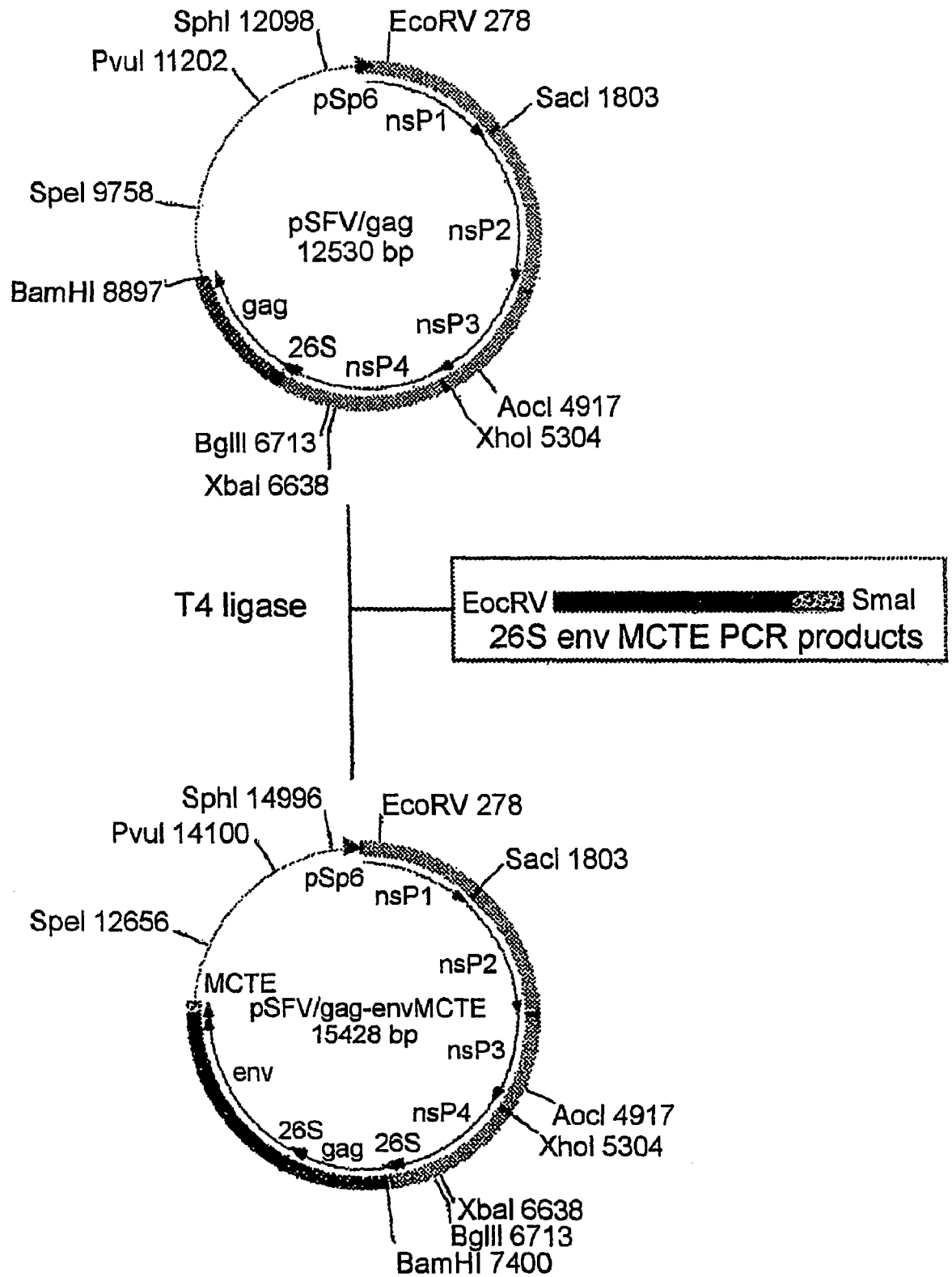
FIG. 28 is a schematic diagram showing a process for construction of an expression vector pSFV/gag-envMCTE.
Figure 29:
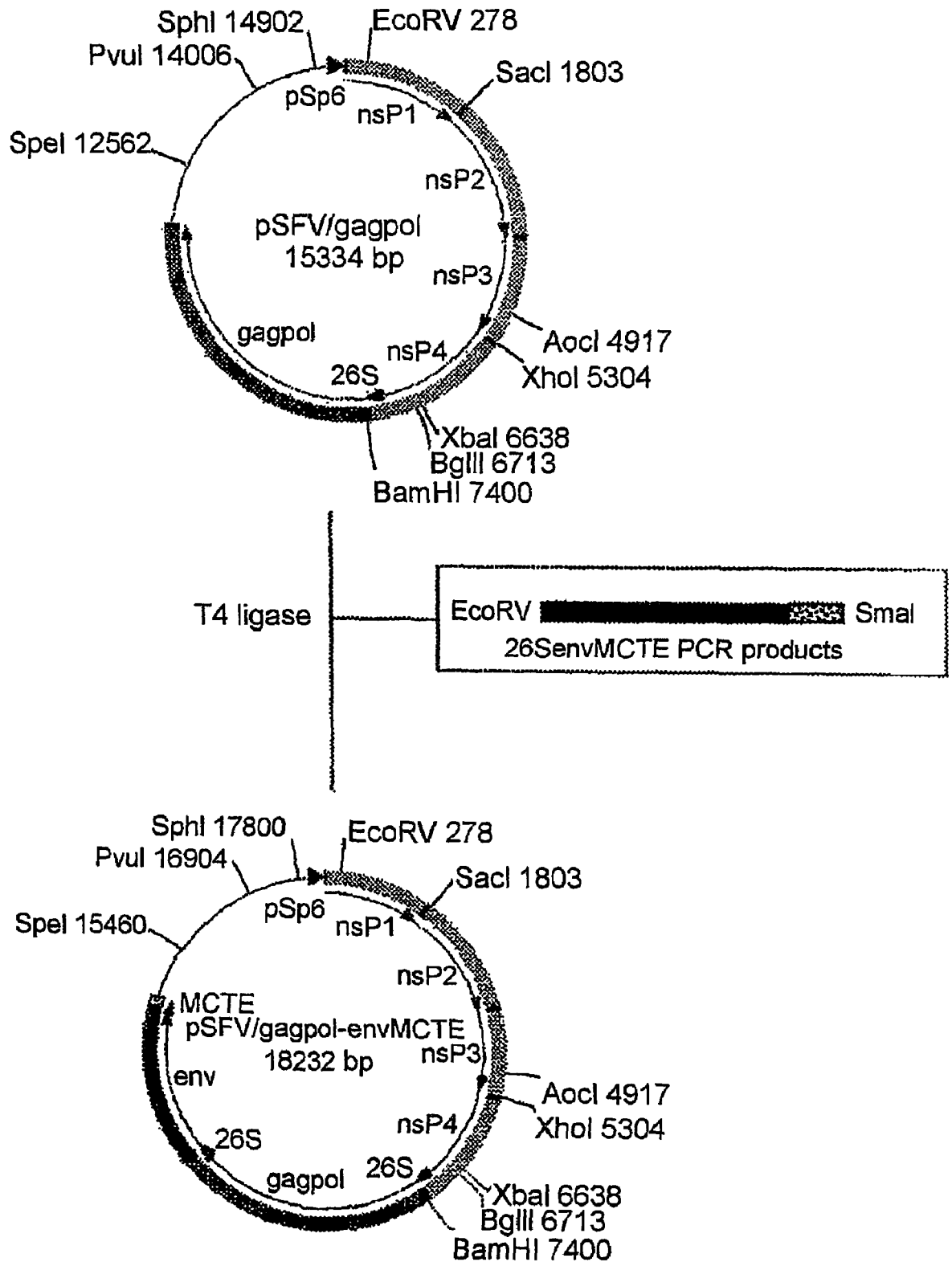
FIG. 29 is a schematic diagram showing a process for construction of an expression vector pSFV/gagpol-envMCTE.

To produce mature VLP carrying Env protein, an env gene containing 26S subgenomic promoter and MCTE was amplified and inserted into a SmaI site of the vector pSFV/gagpol, giving pSFV/gagpol-envMCTE vector. Also, a comparative construct, pSFV/gag-envMCTE vector was prepared. To construct pSFV/gag-envMCTE vector, primarily, pSFV/gag vector was newly prepared. Because the vector pSFV/gag made in Example 1 contains a SmaI site in front of the gag gene, a full-length gag gene (832-2328 bp) of HIV-1 was again amplified by PCR using Primer 18 without SmaI site and Primer 2 according to the same method as Example 1. Next, pSFV/envMCTE (refer to FIG. 27) was prepared by inserting an env gene at a BamHI site of pSFV/MCTE according to the same method as Example 4. 26SenvMCTE was amplified by using pSFV/envMCTE as a template with Primer 12 (sense) for 26S subgenomic promoter and Primer 15 (antisense) for MCTE, and inserted into a SmaI site of pSFV/gag vector, finally giving pSFV/gag-envMCTE (Refer to FIG. 28). Also, the amplified 26SenvMCTE gene was inserted into SmaI site of the vector pSFV/gagpol, giving pSFV/gagpol-envMCTE vector (refer to FIG. 29). The vector pSFV/gagpol-envMCTE was deposited with Korean Culture Center of Microorganisms (KCCM), 361-221, Yurim B/D, Hongie-1-dong, Seodaemun-gu, Seoul 120-091, Republic of Korea, one of international depository authorities, on Dec. 21, 2001, as Accession No. KCCM-10348, under the Budapest Treaty on the International Recognition of the Deposit of Microorganisms for the Purposes of Patent Procedure.

EXAMPLE 17

Figure 30:
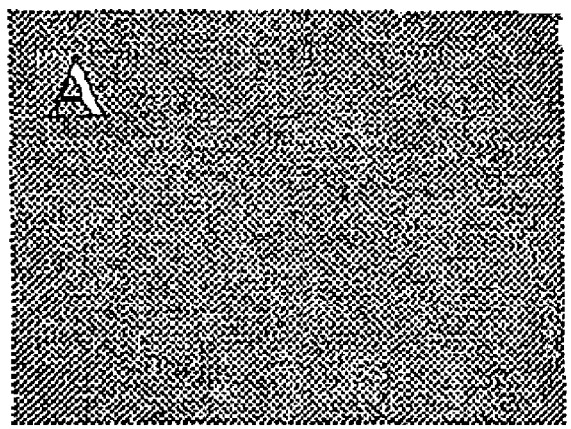
FIG. 30 is a photography for immunocytochemistry showing expression of Gag and Env proteins in BHK-21 cells transfected with pSFV/gag-envMCTE vector, with the use of an anti-p24 polyclonal antibody and an anti-protease polyclonal antibody.
Figure 30:
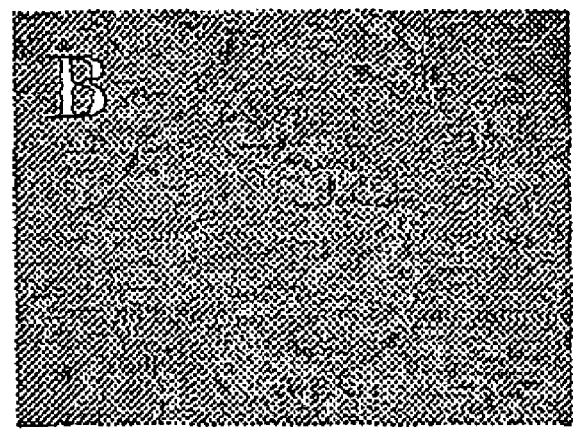
Figure 30:
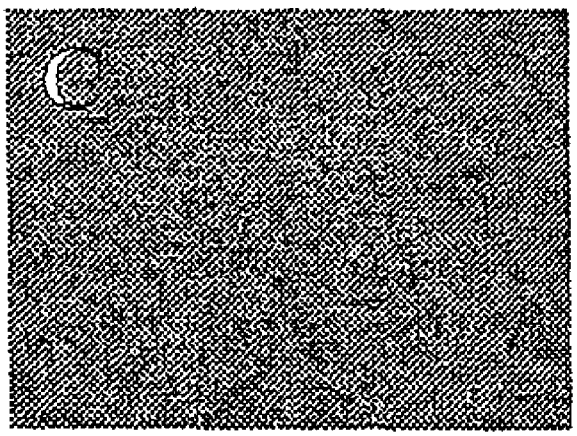
Figure 30:
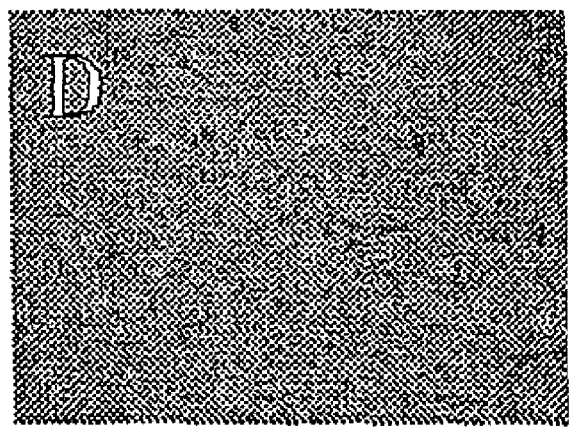

Production of VLP using pSFV/gag-envMCTE and pSFV/gagpol-envMCTE Expression Vectors pSFV/gag-envMCTe was in vitro transcribed, and the transcript was transfected into the BHK-21 cells without pSFV-helper RNA transcripts according to the same method as Example 2. The transfected cells were fixed with cold absolute methanol, cooled at −20° C., for 4 to 6 min, blocked with 1% gelatine, and immunostained with AIDS patient serum, anti-p24 polyclonal antibody, anti-pro polyclonal antibody and anti-env monoclonal antibody (refer to FIG. 30, A: a negative control; B: AIDS patient serum; C: anti-p24 polyclonal antibody; D: anti-env polyclonal antibody). It was found that Env protein as well as Gag protein was expressed in the transfected cells.

Figure 31:
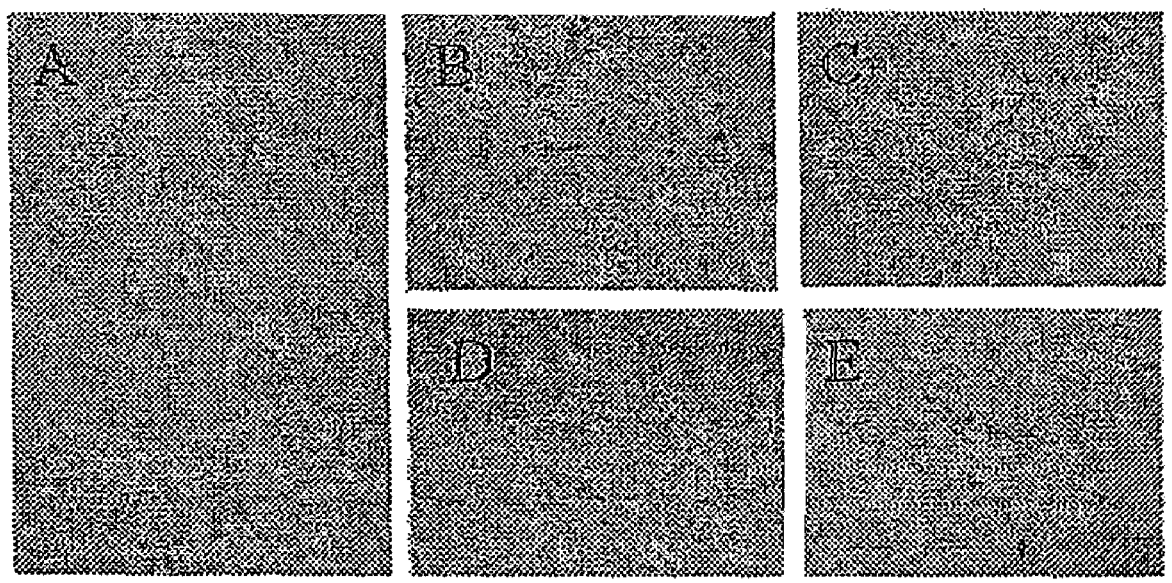
FIG. 31 is a photography for immunocytochemistry showing expression of Gagpol polyprotein and Env protein in BHK-21 cells transfected with pSFV/gagpol-envMCTE vector, with the use of an anti-p24 polyclonal antibody, an anti-protease polyclonal antibody, and an anti-env monoclonal antibody.
Figure 32:
FIG. 32 is a photograph for Western blotting in BHK-21 cells transfected with RNA transcripts of pSFV/gag-envMCTE and pSFV/gagpol-envMCTE, with the use of an anti-p24 polyclonal antibody, and an anti-env monoclonal antibody.
Figure 32:
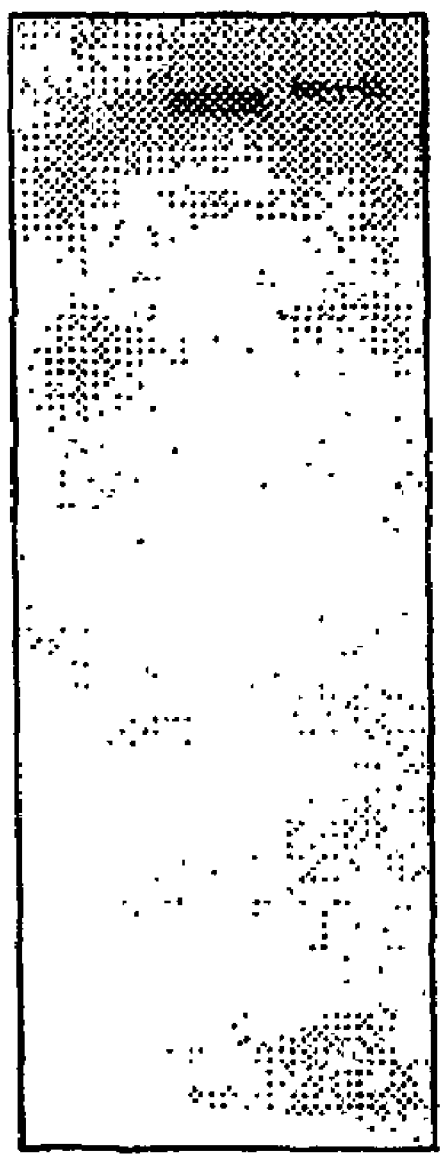

Also, a pSFV/gagpol-envMCTE vector was transfected using the same method as Example 2 (refer to FIG. 31, A: a negative control; B: AIDS patient serum; C: anti-p24 polyclonal antibody; D: anti-pro polyclonal antibody; E: anti-env monoclonal antibody). It was also reveled that Env protein as well as Gagpol protein was expressed in the transfected cells. In addition, at 48 hr after transfection of the RNA transcripts of pSFV/gag-envMCTE and pSFV/gagpol-envMCTE into the BHK-21 cells, VLPs isolated from supernatant of the cultivated medium were analyzed by Western blotting with anti-p24 polyclonal antibody and anti-env monoclonal antibody, followed by ECL assay (refer to FIG. 32, A: AIDS patient serum; B: anti-env monoclonal antibody; lanes 1, and 4: sample from pSFV/gag; lanes 2, and 5: sample from pSFV/gag-envMCTE; lanes 3, and 6: sample from pSFV/gagpol-envMCTE). As a result, it was discovered that, when pSFV/gagpol-envMCTE expressed, there were produced processed mature VLPs carrying Env protein.

What is claimed is:

1. An SFV-based expression vector, comprising nucleotide sequence (6264-8879 bp) of HIV env, operably linked to a first subgenomic promoter, the nucleotide sequence (832-2328 bp) of HIV gag, operably linked to a second subgenomic promoter, and the nucleotide sequence (832-2577 bp) of HIV gagpro, operably linked to a third subgenomic promoter.

2. The SFV-based expression vector as set forth in claim 1, which is plasmid pSFV/env-gag-gagpro.

3. The SFV-based expression vector as set forth in claim 1, which is plasmid pSFV/env-gag-gagΔpro.

4. The SFV-based expression vector as set forth in claim 1, which further comprises a constitutive transport element (CTE).

5. The SFV-based expression vector as set forth in claim 4, which is plasmid pSFV/env-gag-gagpro-CTE or pSFV/env-gag-gagΔpro-CTE.

6. A method of preparing HIV-like particles, comprising the steps of introducing the SFV-based expression vector of claim 1 or its RNA transcript into animal cells, and allowing the expression vector and the RNA to produce HIV-like particles.

7. A host cell transformed with the SFV-based expression vector of claim 1.

8. A composition comprising a sufficient amount of the SFV-based expression vector of claim 1 or its RNA to an induce immune response.

9. A SFV-based expression vector having accession No. KCCM-10233 or KCCM-10234 deposited in the Korean Culture Center of Microorganisms.

10. The vector of claim 9, wherein the accession No. is KCCM-10234.

* * * * *